US 9,895,479 B2

(12) United States Patent
Meyer

(10) Patent No.: US 9,895,479 B2
(45) Date of Patent: Feb. 20, 2018

(54) WATER MANAGEMENT SYSTEM FOR USE IN DIALYSIS

(71) Applicant: Medtronic, Inc., Minneapolis, MN (US)

(72) Inventor: Thomas E. Meyer, Stillwater, MN (US)

(73) Assignee: Medtronic, Inc., Minneapolis, MN (US)

( * ) Notice: Subject to any disclaimer, the term of this patent is extended or adjusted under 35 U.S.C. 154(b) by 25 days.

(21) Appl. No.: 14/566,677

(22) Filed: Dec. 10, 2014

(65) Prior Publication Data

US 2016/0166753 A1 Jun. 16, 2016

(51) Int. Cl.
*A61M 1/16* (2006.01)
*A61M 1/36* (2006.01)

(52) U.S. Cl.
CPC .......... *A61M 1/1682* (2014.02); *A61M 1/169* (2013.01); *A61M 1/1621* (2014.02); *A61M 1/1686* (2013.01); *A61M 1/3652* (2014.02); *A61M 1/1696* (2013.01); *A61M 2205/3317* (2013.01); *A61M 2205/7518* (2013.01)

(58) Field of Classification Search
CPC .............. A61M 1/1682; A61M 1/1621; A61M 1/3652; A61M 1/1686; A61M 1/169; A61M 1/1696
See application file for complete search history.

(56) References Cited

U.S. PATENT DOCUMENTS

| | | |
|---|---|---|
| 3,091,098 A | 5/1963 | Bowers |
| 3,370,710 A | 2/1968 | Bluemle |
| 3,506,126 A | 4/1970 | Lindsay, Jr. |
| 3,608,729 A | 9/1971 | Haselden |
| 3,669,878 A | 6/1972 | Marantz |
| 3,669,880 A | 6/1972 | Marantz |
| 3,692,648 A | 9/1972 | Matloff |
| 3,809,241 A | 5/1974 | Alvine |
| 3,850,835 A | 11/1974 | Marantz |
| 3,884,808 A | 5/1975 | Scott |
| 3,939,069 A | 2/1976 | Granger |
| 3,989,622 A | 11/1976 | Marantz |
| 4,060,485 A | 11/1977 | Eaton |
| 4,094,775 A | 6/1978 | Mueller |
| 4,142,845 A | 3/1979 | Lepp |

(Continued)

FOREIGN PATENT DOCUMENTS

| | | |
|---|---|---|
| CN | 103889481 A1 | 6/2014 |
| DE | 3215003 | 4/1985 |

(Continued)

OTHER PUBLICATIONS

European Search Report for App. No. 15193645.7, dated Apr. 15, 2016.

(Continued)

*Primary Examiner* — Regina M Yoo

(57) ABSTRACT

A water management system for use in dialysis. The water management system includes apparatuses to generate purified water, and a reservoir for storing the purified water. The reservoir can be connected to a dialysate flow loop and the purified water can be generated, stored, and used for later cleaning and disinfection of the dialysis flow loop and the components thereon.

26 Claims, 6 Drawing Sheets

(56) References Cited

U.S. PATENT DOCUMENTS

| | | | |
|---|---|---|---|
| 4,201,555 A | 5/1980 | Tkach |
| 4,209,392 A | 6/1980 | Wallace |
| 4,269,708 A | 5/1981 | Bonomini |
| 4,316,725 A | 2/1982 | Hovind |
| 4,371,385 A | 2/1983 | Johnson |
| 4,374,382 A | 2/1983 | Markowitz |
| 4,381,999 A | 5/1983 | Boucher |
| 4,430,098 A | 2/1984 | Bowman |
| 4,460,555 A | 7/1984 | Thompson |
| 4,490,135 A | 12/1984 | Troutner |
| 4,556,063 A | 12/1985 | Thompson |
| 4,562,751 A | 1/1986 | Nason |
| 4,581,141 A | 4/1986 | Ash |
| 4,650,587 A | 3/1987 | Polak |
| 4,678,408 A | 7/1987 | Mason |
| 4,685,903 A | 8/1987 | Cable |
| 4,695,385 A | 9/1987 | Boag |
| 4,715,398 A | 12/1987 | Shouldice |
| 4,750,494 A | 6/1988 | King |
| 4,826,663 A | 5/1989 | Alberti |
| 4,828,693 A | 5/1989 | Lindsay |
| 4,885,001 A | 12/1989 | Leppert |
| 4,900,308 A | 2/1990 | Verkaart |
| 4,915,713 A | 4/1990 | Buzza |
| 4,977,888 A * | 12/1990 | Rietter | A61B 17/2251 601/4 |
| 5,080,653 A | 1/1992 | Voss |
| 5,092,886 A | 3/1992 | Dobos-Hardy |
| 5,097,122 A | 3/1992 | Coiman |
| 5,114,580 A | 5/1992 | Ahmad |
| 5,127,404 A | 7/1992 | Wyborny |
| 5,180,403 A | 1/1993 | Kogure |
| 5,284,470 A | 2/1994 | Beltz |
| 5,302,288 A | 4/1994 | Meidl |
| 5,305,745 A | 4/1994 | Zacouto |
| 5,318,750 A | 6/1994 | Lascombes |
| 5,419,347 A * | 5/1995 | Carruth | A61G 7/02 134/113 |
| 5,468,388 A | 11/1995 | Goddard et al. |
| 5,591,344 A | 1/1997 | Kenley |
| 5,683,432 A | 11/1997 | Goedeke |
| 5,685,835 A * | 11/1997 | Brugger | A61M 1/168 210/646 |
| 5,702,536 A * | 12/1997 | Carruth | A61G 7/02 134/10 |
| 5,744,031 A | 4/1998 | Bene |
| 5,762,782 A | 6/1998 | Kenley |
| 5,863,421 A | 1/1999 | Peter |
| 5,938,938 A | 8/1999 | Bosetto |
| 5,944,684 A | 8/1999 | Roberts |
| 5,948,251 A * | 9/1999 | Brugger | A61M 1/168 210/175 |
| 6,048,732 A | 4/2000 | Anslyn |
| 6,052,622 A | 4/2000 | Holmstrom |
| 6,058,331 A | 5/2000 | King |
| 6,230,059 B1 | 5/2001 | Duffin |
| 6,248,093 B1 | 6/2001 | Moberg |
| 6,251,167 B1 | 6/2001 | Berson |
| 6,254,567 B1 | 7/2001 | Treu |
| 6,264,680 B1 | 7/2001 | Ash |
| 6,321,101 B1 | 11/2001 | Holmstrom |
| 6,362,591 B1 | 3/2002 | Moberg |
| 6,363,279 B1 | 3/2002 | Ben-Haim |
| 6,554,798 B1 | 4/2003 | Mann |
| 6,555,986 B2 | 4/2003 | Moberg |
| 6,589,229 B1 | 7/2003 | Connelly |
| 6,602,399 B1 | 8/2003 | Fromherz |
| 6,627,164 B1 | 9/2003 | Wong |
| 6,676,608 B1 | 1/2004 | Keren |
| 6,711,439 B1 | 3/2004 | Bradley |
| 6,726,647 B1 | 4/2004 | Sternby |
| 6,780,322 B1 | 8/2004 | Bissler |
| 6,814,724 B2 | 11/2004 | Taylor |
| 6,818,196 B2 | 11/2004 | Wong |
| 6,824,524 B1 | 11/2004 | Favre |
| 6,878,283 B2 | 4/2005 | Thompson |
| 6,960,179 B2 | 11/2005 | Gura |
| 7,023,359 B2 | 4/2006 | Goetz |
| 7,074,332 B2 | 7/2006 | Summerton |
| 7,077,819 B1 | 7/2006 | Goldau |
| 7,169,303 B2 | 1/2007 | Sullivan |
| 7,208,092 B2 | 4/2007 | Micheli |
| 7,241,272 B2 | 7/2007 | Karoor |
| 7,276,042 B2 | 10/2007 | Polaschegg |
| 7,279,031 B1 | 10/2007 | Wright |
| 7,500,958 B2 | 3/2009 | Asbrink |
| 7,566,432 B2 | 7/2009 | Wong |
| 7,575,564 B2 | 8/2009 | Childers |
| 7,597,806 B2 | 10/2009 | Uchi |
| 7,674,231 B2 | 3/2010 | McCombie |
| 7,704,361 B2 | 4/2010 | Garde |
| 7,736,507 B2 | 6/2010 | Wong |
| 7,744,553 B2 | 6/2010 | Kelly |
| 7,754,852 B2 | 7/2010 | Burnett |
| 7,756,572 B1 | 7/2010 | Fard |
| 7,776,210 B2 | 8/2010 | Rosenbaum |
| 7,785,463 B2 | 8/2010 | Bissler |
| 7,790,103 B2 * | 9/2010 | Shah | A61L 2/183 422/28 |
| 7,794,141 B2 | 9/2010 | Perry |
| 7,850,635 B2 | 12/2010 | Polaschegg |
| 7,857,976 B2 | 12/2010 | Bissler |
| 7,867,214 B2 | 1/2011 | Childers |
| 7,896,831 B2 | 3/2011 | Sternby |
| 7,922,686 B2 | 4/2011 | Childers |
| 7,922,911 B2 | 4/2011 | Micheli |
| 7,947,179 B2 | 5/2011 | Rosenbaum |
| 7,955,291 B2 | 6/2011 | Sternby |
| 7,967,022 B2 | 6/2011 | Grant |
| 7,981,082 B2 | 7/2011 | Wang |
| 8,002,726 B2 | 8/2011 | Karoor |
| 8,034,161 B2 | 10/2011 | Gura |
| 8,070,709 B2 | 12/2011 | Childers |
| 8,096,969 B2 | 1/2012 | Roberts |
| 8,183,046 B2 | 5/2012 | Lu |
| 8,187,250 B2 | 5/2012 | Roberts |
| 8,197,439 B2 | 6/2012 | Wang |
| 8,202,241 B2 | 6/2012 | Karakama |
| 8,246,826 B2 | 8/2012 | Wilt |
| 8,273,049 B2 | 9/2012 | Demers |
| 8,292,594 B2 | 10/2012 | Tracey |
| 8,313,642 B2 | 11/2012 | Yu |
| 8,317,492 B2 | 11/2012 | Demers |
| 8,357,113 B2 | 1/2013 | Childers |
| 8,366,316 B2 | 2/2013 | Kamen |
| 8,366,655 B2 | 2/2013 | Kamen |
| 8,409,441 B2 * | 4/2013 | Wilt | B01D 61/32 210/636 |
| 8,449,448 B2 | 5/2013 | Hovland |
| 8,491,517 B2 | 7/2013 | Karoor |
| 8,496,809 B2 | 7/2013 | Roger |
| 8,499,780 B2 | 8/2013 | Wilt |
| 8,500,672 B2 | 8/2013 | Caleffi |
| 8,500,676 B2 | 8/2013 | Jansson |
| 8,500,994 B2 | 8/2013 | Weaver |
| 8,512,271 B2 | 8/2013 | Moissl |
| 8,518,258 B2 | 8/2013 | Balschat |
| 8,518,260 B2 | 8/2013 | Raimann |
| 8,521,482 B2 | 8/2013 | Akonur |
| 8,535,525 B2 | 9/2013 | Heyes |
| 8,560,510 B2 | 10/2013 | Brueggerhoff |
| 8,562,822 B2 | 10/2013 | Roger |
| 8,580,112 B2 | 11/2013 | Updyke |
| 8,597,227 B2 | 12/2013 | Childers |
| 8,696,626 B2 | 4/2014 | Kirsch |
| 8,903,492 B2 | 12/2014 | Soykan |
| 8,906,240 B2 | 12/2014 | Crnkovich |
| 2002/0042561 A1 | 4/2002 | Schulman |
| 2002/0045851 A1 | 4/2002 | Suzuki |
| 2002/0104800 A1 | 8/2002 | Collins |
| 2002/0112609 A1 | 8/2002 | Wong |
| 2003/0010717 A1 | 1/2003 | Brugger |
| 2003/0080059 A1 | 5/2003 | Peterson |

(56) References Cited

U.S. PATENT DOCUMENTS

| | | |
|---|---|---|
| 2003/0097086 A1 | 5/2003 | Gura |
| 2003/0105435 A1 | 6/2003 | Taylor |
| 2003/0114787 A1 | 6/2003 | Gura |
| 2004/0019312 A1 | 1/2004 | Childers |
| 2004/0068219 A1 | 4/2004 | Summerton |
| 2004/0082903 A1 | 4/2004 | Micheli |
| 2004/0099593 A1 | 5/2004 | DePaolis |
| 2004/0143173 A1 | 7/2004 | Reghabi |
| 2004/0147900 A1 | 7/2004 | Polaschegg |
| 2004/0168969 A1 | 9/2004 | Sternby |
| 2004/0215090 A1 | 10/2004 | Erkkila |
| 2005/0065760 A1 | 3/2005 | Murtfeldt |
| 2005/0113796 A1 | 5/2005 | Taylor |
| 2005/0115898 A1 | 6/2005 | Sternby |
| 2005/0126961 A1 | 6/2005 | Bissler |
| 2005/0131331 A1 | 6/2005 | Kelly |
| 2005/0131332 A1 | 6/2005 | Kelly |
| 2005/0126998 A1 | 7/2005 | Childers |
| 2005/0150832 A1 | 7/2005 | Tsukamoto |
| 2005/0234381 A1 | 10/2005 | Niemetz |
| 2005/0274658 A1 | 12/2005 | Rosenbaum |
| 2006/0025661 A1 | 2/2006 | Sweeney |
| 2006/0217771 A1 | 2/2006 | Soykan |
| 2006/0054489 A1 | 3/2006 | Denes |
| 2006/0076295 A1 | 4/2006 | Leonard |
| 2006/0157335 A1 | 7/2006 | Levine |
| 2006/0157413 A1 | 7/2006 | Bene |
| 2006/0195064 A1 | 8/2006 | Plahey |
| 2006/0226079 A1 | 10/2006 | Mori |
| 2006/0241709 A1 | 10/2006 | Soykan |
| 2006/0264894 A1 | 11/2006 | Moberg |
| 2007/0007208 A1 | 1/2007 | Brugger |
| 2007/0066928 A1 | 3/2007 | Lannoy |
| 2007/0072285 A1 * | 3/2007 | Barringer, Jr. ........ B01D 61/142 435/286.5 |
| 2007/0138011 A1 | 6/2007 | Hofmann |
| 2007/0175827 A1 | 8/2007 | Wariar |
| 2007/0179431 A1 | 8/2007 | Roberts |
| 2007/0213653 A1 | 9/2007 | Childers |
| 2007/0213665 A1 | 9/2007 | Curtin |
| 2007/0215545 A1 | 9/2007 | Bissler |
| 2007/0255250 A1 | 11/2007 | Moberg |
| 2008/0006570 A1 | 1/2008 | Gura |
| 2008/0021337 A1 | 1/2008 | Li |
| 2008/0053905 A9 | 3/2008 | Brugger |
| 2008/0067132 A1 | 3/2008 | Ross |
| 2008/0093276 A1 | 4/2008 | Roger |
| 2008/0154543 A1 * | 6/2008 | Rajagopal ............... G01N 35/00 702/183 |
| 2008/0215247 A1 | 9/2008 | Tonelli |
| 2008/0230473 A1 | 9/2008 | Herbst |
| 2008/0253427 A1 | 10/2008 | Kamen |
| 2009/0012450 A1 * | 1/2009 | Shah ..................... A61L 2/183 604/29 |
| 2009/0020471 A1 | 1/2009 | Tsukamoto |
| 2009/0078636 A1 | 3/2009 | Uchi |
| 2009/0084721 A1 | 4/2009 | Yardimci |
| 2009/0101549 A1 | 4/2009 | Kamen |
| 2009/0101577 A1 | 4/2009 | Fulkerson |
| 2009/0105629 A1 | 4/2009 | Grant |
| 2009/0124963 A1 | 5/2009 | Hogard |
| 2009/0127193 A1 | 5/2009 | Updyke |
| 2009/0131858 A1 | 5/2009 | Fissell |
| 2009/0157877 A1 | 6/2009 | Baek |
| 2009/0171261 A1 | 7/2009 | Sternby |
| 2009/0182263 A1 * | 7/2009 | Burbank ............ A61M 1/1656 604/28 |
| 2009/0187138 A1 | 7/2009 | Lundtveit |
| 2009/0216045 A1 | 8/2009 | Singh |
| 2009/0223539 A1 * | 9/2009 | Gibbel .................. H01L 31/18 134/2 |
| 2009/0275849 A1 | 11/2009 | Stewart |
| 2009/0275883 A1 | 11/2009 | Chapman |
| 2009/0281484 A1 | 11/2009 | Childers |
| 2009/0282980 A1 | 11/2009 | Gura |
| 2009/0314063 A1 | 12/2009 | Sternby |
| 2010/0004588 A1 | 1/2010 | Yeh |
| 2010/0007838 A1 | 1/2010 | Fujimoto |
| 2010/0010429 A1 | 1/2010 | Childers |
| 2010/0022936 A1 | 1/2010 | Gura |
| 2010/0030151 A1 | 2/2010 | Kirsch |
| 2010/0042035 A1 | 2/2010 | Moissl |
| 2010/0078381 A1 | 4/2010 | Merchant |
| 2010/0078387 A1 | 4/2010 | Wong |
| 2010/0084330 A1 | 4/2010 | Wong |
| 2010/0087771 A1 | 4/2010 | Karakama |
| 2010/0094158 A1 | 4/2010 | Solem |
| 2010/0100027 A1 | 4/2010 | Schilthuizen |
| 2010/0114012 A1 | 5/2010 | Sandford |
| 2010/0130906 A1 | 5/2010 | Balschat |
| 2010/0137693 A1 | 6/2010 | Porras |
| 2010/0137782 A1 | 6/2010 | Jansson |
| 2010/0140149 A1 | 6/2010 | Fulkerson |
| 2010/0168546 A1 | 7/2010 | Kamath |
| 2010/0192686 A1 * | 8/2010 | Kamen .................. A61M 1/16 73/290 R |
| 2010/0199670 A1 | 8/2010 | Robertson |
| 2010/0217180 A1 | 8/2010 | Akonur |
| 2010/0217181 A1 | 8/2010 | Roberts |
| 2010/0224492 A1 | 9/2010 | Ding |
| 2010/0234795 A1 | 9/2010 | Wallenas |
| 2010/0241045 A1 | 9/2010 | Kelly |
| 2010/0274171 A1 | 10/2010 | Caleffi |
| 2010/0312174 A1 | 12/2010 | Hoffman |
| 2010/0326911 A1 | 12/2010 | Rosenbaum |
| 2010/0327586 A1 | 12/2010 | Mardirossian |
| 2011/0009798 A1 | 1/2011 | Kelly |
| 2011/0017665 A1 | 1/2011 | Updyke |
| 2011/0048949 A1 | 3/2011 | Ding et al. |
| 2011/0066043 A1 | 3/2011 | Banet |
| 2011/0071465 A1 | 3/2011 | Wang |
| 2011/0077574 A1 | 3/2011 | Sigg |
| 2011/0079558 A1 | 4/2011 | Raimann |
| 2011/0087187 A1 | 4/2011 | Beck |
| 2011/0100909 A1 | 5/2011 | Stange |
| 2011/0105983 A1 | 5/2011 | Kelly |
| 2011/0106003 A1 | 5/2011 | Childers |
| 2011/0120946 A1 | 5/2011 | Levin |
| 2011/0130666 A1 | 6/2011 | Dong |
| 2011/0132838 A1 | 6/2011 | Curtis |
| 2011/0144570 A1 | 6/2011 | Childers |
| 2011/0160637 A1 | 6/2011 | Beiriger |
| 2011/0163030 A1 | 7/2011 | Weaver |
| 2011/0163034 A1 | 7/2011 | Castellarnau |
| 2011/0184340 A1 | 7/2011 | Tan |
| 2011/0189048 A1 | 8/2011 | Curtis |
| 2011/0220562 A1 | 9/2011 | Beiriger |
| 2011/0272337 A1 | 11/2011 | Palmer |
| 2011/0315611 A1 * | 12/2011 | Fulkerson ........... A61M 1/3639 210/96.2 |
| 2012/0006762 A1 | 1/2012 | McCabe |
| 2012/0016228 A1 | 1/2012 | Kroh |
| 2012/0031825 A1 | 2/2012 | Gura |
| 2012/0083729 A1 | 4/2012 | Childers |
| 2012/0085707 A1 | 4/2012 | Beiriger |
| 2012/0115248 A1 | 5/2012 | Ansyln |
| 2012/0220528 A1 | 8/2012 | VanAntwerp |
| 2012/0258545 A1 | 10/2012 | Ash |
| 2012/0258546 A1 | 10/2012 | Marran |
| 2012/0259276 A1 | 10/2012 | Childers |
| 2012/0273354 A1 | 11/2012 | Orhan et al. |
| 2012/0273415 A1 | 11/2012 | Gerber |
| 2012/0273420 A1 | 11/2012 | Gerber |
| 2012/0277546 A1 | 11/2012 | Soykan |
| 2012/0277551 A1 | 11/2012 | Gerber |
| 2012/0277552 A1 | 11/2012 | Gerber |
| 2012/0277604 A1 | 11/2012 | Gerber |
| 2012/0277650 A1 | 11/2012 | Gerber |
| 2012/0277655 A1 | 11/2012 | Gerber |
| 2012/0277722 A1 | 11/2012 | Gerber |
| 2012/0302945 A1 | 11/2012 | Hedmann |
| 2013/0018301 A1 | 1/2013 | Weaver |
| 2013/0019994 A1 | 1/2013 | Schaer |

(56) References Cited

U.S. PATENT DOCUMENTS

| | | |
|---|---|---|
| 2013/0037465 A1 | 2/2013 | Heyes |
| 2013/0193073 A1 | 8/2013 | Hogard |
| 2013/0199998 A1 | 8/2013 | Kelly |
| 2013/0211730 A1 | 8/2013 | Wolff |
| 2013/0213890 A1 | 8/2013 | Kelly |
| 2013/0228516 A1 | 9/2013 | Jonsson |
| 2013/0228517 A1 | 9/2013 | Roger |
| 2013/0231607 A1 | 9/2013 | Roger |
| 2013/0248426 A1 | 9/2013 | Pouchoulin |
| 2013/0256227 A1 | 10/2013 | Kelly |
| 2013/0274642 A1 | 10/2013 | Soykan |
| 2013/0304020 A1* | 11/2013 | Wilt ............ A61M 1/16 604/506 |
| 2013/0324915 A1 | 12/2013 | (Krensky)Britton |
| 2013/0330208 A1 | 12/2013 | Ly |
| 2013/0331774 A1 | 12/2013 | Farrell |
| 2014/0001112 A1 | 1/2014 | Karoor |
| 2014/0018728 A1 | 1/2014 | Plahey |
| 2014/0042092 A1 | 2/2014 | Akonur |
| 2014/0065950 A1 | 3/2014 | Mendelsohn |
| 2014/0088442 A1 | 3/2014 | Soykan |
| 2014/0110340 A1 | 4/2014 | White |
| 2014/0110341 A1 | 4/2014 | White |
| 2014/0158538 A1 | 6/2014 | Collier |
| 2014/0158588 A1 | 6/2014 | Pudil |
| 2014/0158623 A1 | 6/2014 | Pudil |
| 2014/0190876 A1 | 7/2014 | Meyer |
| 2014/0216250 A1* | 8/2014 | Meyer ............ A61M 1/1658 95/22 |
| 2014/0217020 A1 | 8/2014 | Meyer |
| 2014/0217027 A1 | 8/2014 | Meyer |
| 2014/0217028 A1 | 8/2014 | Pudil |
| 2014/0217029 A1 | 8/2014 | Meyer |
| 2014/0217030 A1 | 8/2014 | Meyer |
| 2014/0220699 A1 | 8/2014 | Pudil |
| 2014/0224736 A1 | 8/2014 | Heide |
| 2015/0057602 A1 | 2/2015 | Mason |
| 2015/0083647 A1* | 3/2015 | Meyer ............ A61M 1/1656 210/85 |
| 2015/0114891 A1* | 4/2015 | Meyer ............ A61M 1/3465 210/85 |
| 2015/0144539 A1 | 5/2015 | Pudil |
| 2016/0038666 A1 | 2/2016 | Kelly |
| 2016/0166748 A1 | 6/2016 | Meyer |
| 2016/0166751 A1 | 6/2016 | Meyer |
| 2016/0166752 A1 | 6/2016 | Meyer |
| 2016/0166753 A1 | 6/2016 | Meyer |

FOREIGN PATENT DOCUMENTS

| | | |
|---|---|---|
| DE | 102011052188 | 1/2013 |
| EP | 0022370 A1 | 1/1981 |
| EP | 0187109 | 7/1986 |
| EP | 266795 A2 | 11/1987 |
| EP | 0298587 | 6/1994 |
| EP | 0743071 | 11/1996 |
| EP | 1124599 | 5/2000 |
| EP | 1175238 | 11/2000 |
| EP | 2308526 | 10/2003 |
| EP | 1364666 A1 | 11/2003 |
| EP | 1523347 | 1/2004 |
| EP | 1523350 | 1/2004 |
| EP | 0906768 B1 | 2/2004 |
| EP | 1691863 | 4/2005 |
| EP | 2116269 | 2/2008 |
| EP | 1450879 | 10/2008 |
| EP | 1514562 | 4/2009 |
| EP | 2219703 | 5/2009 |
| EP | 1592494 B1 | 6/2009 |
| EP | 1490129 | 9/2009 |
| EP | 2100553 A1 | 9/2009 |
| EP | 2398529 | 11/2010 |
| EP | 2575827 A2 | 12/2010 |
| EP | 2100553 | 8/2011 |
| EP | 2388030 | 11/2011 |
| EP | 2576453 A2 | 12/2011 |
| EP | 2701580 | 11/2012 |
| EP | 2701595 | 11/2012 |
| EP | 1345856 B1 | 3/2013 |
| EP | 2344220 B1 | 4/2013 |
| EP | 1351756 | 7/2013 |
| EP | 2190498 | 7/2013 |
| EP | 1414543 | 9/2013 |
| EP | 2701596 | 3/2014 |
| EP | 1787666 | 11/2015 |
| FR | 2237639 | 2/1977 |
| JP | 2002306904 | 10/2002 |
| JP | 5099464 | 10/2012 |
| WO | 1996040313 | 12/1996 |
| WO | 9937342 | 7/1999 |
| WO | 0057935 | 10/2000 |
| WO | 2000066197 | 11/2000 |
| WO | 2001085295 A2 | 9/2001 |
| WO | 200066197 A1 | 11/2001 |
| WO | 2003043677 A2 | 5/2003 |
| WO | 2003043680 | 5/2003 |
| WO | 2003051422 A2 | 6/2003 |
| WO | 2004008826 | 1/2004 |
| WO | 2004009156 | 1/2004 |
| WO | 200170307 A1 | 4/2004 |
| WO | 2004030716 A2 | 4/2004 |
| WO | 2004030717 A2 | 4/2004 |
| WO | 2004064616 A2 | 8/2004 |
| WO | 2004105589 A2 | 12/2004 |
| WO | 2005044339 | 5/2005 |
| WO | 2004105589 A3 | 6/2005 |
| WO | 2005061026 | 7/2005 |
| WO | 2005123230 A2 | 12/2005 |
| WO | 2006023589 | 3/2006 |
| WO | 2007010164 A2 | 1/2007 |
| WO | 2007089855 A2 | 8/2007 |
| WO | 2007146162 A2 | 12/2007 |
| WO | 2007146162 A3 | 12/2007 |
| WO | 2008037410 | 4/2008 |
| WO | 2009026603 | 12/2008 |
| WO | 2009024566 | 2/2009 |
| WO | 2009026603 A1 | 3/2009 |
| WO | 2009061608 | 5/2009 |
| WO | 2009064984 | 5/2009 |
| WO | 2009071103 | 6/2009 |
| WO | 2009094184 | 7/2009 |
| WO | 2009132839 A1 | 11/2009 |
| WO | 2009157877 A1 | 12/2009 |
| WO | 2009157878 A1 | 12/2009 |
| WO | 2010028860 A1 | 2/2010 |
| WO | 2010028860 | 3/2010 |
| WO | 2010042666 | 4/2010 |
| WO | 2010042666 A2 | 4/2010 |
| WO | 2010052705 A1 | 5/2010 |
| WO | 2010062698 | 6/2010 |
| WO | 2010096659 | 10/2010 |
| WO | 2010121820 | 10/2010 |
| WO | 2011017215 A1 | 2/2011 |
| WO | 2011025705 A1 | 3/2011 |
| WO | 2012026978 | 3/2012 |
| WO | 2012042323 | 4/2012 |
| WO | 2012050781 | 4/2012 |
| WO | 2012051996 | 4/2012 |
| WO | 2012067585 | 5/2012 |
| WO | 2010042666 A3 | 6/2012 |
| WO | 2012148781 | 11/2012 |
| WO | 2012148786 | 11/2012 |
| WO | 2012148789 | 11/2012 |
| WO | 2012162515 A2 | 11/2012 |
| WO | 2012172398 | 12/2012 |
| WO | 2013019179 A1 | 2/2013 |
| WO | 2013019994 A2 | 2/2013 |
| WO | 2013025844 | 2/2013 |
| WO | 2013025844 A2 | 2/2013 |
| WO | 2013027214 | 2/2013 |
| WO | 2013028809 A2 | 2/2013 |
| WO | 2013028809 A3 | 2/2013 |
| WO | 2013019994 A3 | 4/2013 |

(56) References Cited

FOREIGN PATENT DOCUMENTS

| WO | 2013025844 A3 | 5/2013 |
|---|---|---|
| WO | 2013103607 A1 | 7/2013 |
| WO | 2013103906 | 7/2013 |
| WO | 2013110906 | 8/2013 |
| WO | 2013110919 | 8/2013 |
| WO | 2013114063 A1 | 8/2013 |
| WO | 2013121162 A1 | 8/2013 |
| WO | 2013140346 | 9/2013 |
| WO | 2013141896 | 9/2013 |
| WO | 2013188861 A1 | 12/2013 |
| WO | 14066254 | 5/2014 |
| WO | 14066255 | 5/2014 |
| WO | 14077082 | 5/2014 |
| WO | 14117000 | 7/2014 |
| WO | 2014121162 | 8/2014 |
| WO | 2014121163 | 8/2014 |
| WO | 2014121167 | 8/2014 |
| WO | 2014121169 | 8/2014 |

OTHER PUBLICATIONS

Culleton, BF et al. Effect of Frequent Nocturnal Hemodialysis vs. Conventional Hemodialysis on Left Ventricular Mass and Quality of Life. 2007 Journal of the American Medical Association 298 (11), 1291-1299.
Siegenthalar, et al., Pulmonary fluid status monitoring with intrathoracic impedance, Journal of Clinical Monitoring and Computing, 24:449-451, 2010.
Wang, Fundamentals of intrathoracic impedance monitoring in heart failure, Am. J. Cardiology, 2007, 3G-10G: Suppl.
Written Opinion of the International Searching Authority for PCT/US2012/049398 dated Feb. 25, 2013.
Gambro AK 96 Dialysis Machine Operator's Manual, Dec. 2012.
European Search Report 12819714.2-1651/2739325 PCT/US2012049398, dated Jun. 12, 2015.
Roberts M, The regenerative dialysis (REDY) sorbent system. Nephrology, 1998, 275-278:4.
Marchant, et. al., In vivo Biocompatibility Studies 1: The Cage Implant System and a Biodegradable Hydrogel, J. Biomed. Mat. Res., 1983, 301-325: 17.
Bleyer, et al, Kidney International. Jun. 2006; 69(12):2268-2273.
PCT/US2012/025711, International Search Report dated Jul. 4, 2012.
International Search Report from PCT/US2012/051946.
PCT/US2012/051011, International Search Report, dated Jan. 17, 2014.
PCT Application, PCT/US20013/020404, dated Jan. 4, 2013.
U.S. Appl. No. 13/836,973, filed Mar. 15, 2013.
U.S. Appl. No. 14/259,655, filed Apr. 23, 2014.
U.S. Appl. No. 14/259,589, filed Apr. 23, 2014.
U.S. Appl. No. 13/757,693, filed Feb. 1, 2013.
PCT/US2014/14343 Int'l Search Report & Written Opinion, dated Sep. 2006.
EP 14746791 Supplementary European Search Report dated Aug. 19, 2016.
PCT/US2014/014350 International Search Report and Written Opinion dated May 2014.
EP 14746793 Supplementary European Search Report dated Aug. 18, 2016.
U.S. Appl. No. 29/446,285, filed Feb. 1, 2013.
U.S. Appl. No. 61/526,209.
U.S. Appl. No. 13/757,693, filed Jan. 4, 2013.
U.S. Appl. No. 13/836,079, filed Mar. 15, 2013.
U.S. Appl. No. 14/240,129, filed Aug. 22, 2013.
U.S. Appl. No. 13/835,735, filed Mar. 15, 2013.
PCT/US2014/014345 International Search Report and Written Opinion, dated May 2014.
Leifer et al., 'A Study on the Temperature Variation of Rise Velocity for Large Clean Bubbles,' J. Atmospheric & Oceanic Tech., vol. 17, pp. 1392-1402.
Talaia, 'Terminal Velocity of a Bubble Rise in a Liquid Column,' World Acad. of Sci., Engineering & Tech., vol. 28, pp. 264-68.
The FHN Trial Group. In-Center. Hemodialysis Six Times per Week versus Three Times per Week, New England Journal of Medicine, 2010 Abstract.
PCT/US2014/014357 International Search Report and Written Opinion.
U.S. Appl. No. 13/757,722, filed Feb. 1, 2013.
U.S. Appl. No. 13/757,794, filed Feb. 2, 2012.
U.S. Appl. No. 13/791,755, filed Mar. 8, 2013.
U.S. Appl. No. 13/757,792, filed Feb. 2, 2013.
U.S. Appl. No. 13/837,287, filed Mar. 15, 2013.
U.S. Appl. No. 13/757,794, filed Feb. 2, 2013.
Weissman, S., et al., "Hydroxyurea-induced hepatitis in human immunodeficiency virus-positive patients." Clin. Infec. Dis, (Jul. 29, 1999): 223-224.
Maclean, et, al., Effects of hindlimb contraction on pressor and muscle interstitial metabolite responses in the cat, J. App. Physiol., 1998, 1583-1592, 85 (4).
Overgaard, et. al., Activity-induced recovery of excitability in K+-depressed rat soieus muscle, Am. J. P.
Overgaard. et. al., Relations between excitability and contractility in rate soleus'muscle: role of the Na+—K+ pump and NA+—K—S gradients. Journal of Physiology, 1999, 215-225, 518(1).
Wheaton, et al., Dowex Ion Exchange Resins—Fundamentals of Ion Exchange; Jun. 2000, pp. 1-9. http://www.dow.com/scripts/litorder.asp? filepath=liquidseps/pdfs/noreg/177-01837.pdf.
Ronco et al. 2008, 'Cardiorenal Syndrome,' Journal American College Cardiology, 52:1527-1539, Abstract.
U.S. Appl. No. 61/480,544.
PCT/US2014/067650 International Search Report Written Opinion dated Mar. 9, 2015.
Brynda, et. al., The detection of toman 2-microglcbuiin by grating coupler immunosensor with three dimensional antibody networks. Biosensors & Bioelectronics, 1999, 363-368, 14(4).
Hemametrics, Crit-Line Hematocrit Accuracy, 2003, 1-5, vol. 1, Tech Note No. 11 (Rev. D).
Lima, et. al., An electrochemical sensor based on nanostructure hollsndite-type manganese oxide for detection of potassium ion, Sensors, 2009, 6613-8625, 9.
Nedelkov, et. al., Design of buffer exchange surfaces and sensor chips for biosensor chip mass spectrometry, Proteomics, 2002, 441-446, 2(4).
PCT/US/2012/034327, International Search Report, dated Aug. 13, 2013.
PCT/US/2012/034329, International Search Report, dated Dec. 3, 2012.
PCT/US2012/034331, International Search Report, dated Jul. 9, 2012.
PCT/US2012/034332, International Search Report, dated Jul. 5, 2012.
PCT/US2012/034334, International Search Report, dated Jul. 6, 2012.
PCT/US2012/034335, International Search Report, dated Sep. 5, 2012.
Redfield, et. al, Restoration of renal response to atria! natriuretic factor in experimental low-output heat failure, Am. J. Physiol., 1989, R917-923:257.
Rogoza, et. al., Validation of A&D UA-767 device for the self-measurement of blood pressure, Blood Pressure Monitoring, 2000, 227-231, 5(4).
Secemsky, et. al, High prevalence of cardiac autonomic dysfunction and T-wave alternans in dialysis patients. Heart Rhythm, Apr. 2011, 592-598 : vol. 8, No. 4.
Wei, et. al., Fullerene-cryptand coated piezoelectric crystal urea sensor based on urease, Analytica Chimica Acta, 2001,77-85:437.
Zhong, et. al., Miniature urea sensor based on H(+)-ion sensitive field effect transistor and its application in clinical analysis, Chin. J. Biotechnol., 1992, 57-65. 8(1).
Coast, et al. 1990, An approach to Cardiac Arrhythmia analysis Using Hidden Markov Models, IEEE Transactions on Biomedical Engineering. 1990, 37 (9):826-835.
U.S. Appl. No. 13/368,225.

(56) References Cited

OTHER PUBLICATIONS

U.S. Appl. No. 13/424,533.
U.S. Appl. No. 13/424,467.
U.S. Appl. No. 13/424,454.
U.S. Appl. No. 13/424,490.
U.S. Appl. No. 13/424,517.
U.S. Appl. No. 61/480,532.
PCT/US2012/034330, International Preliminary Report on Patentability, dated Oct. 29, 2013.
PCT/US2012/034333, International Preliminary Report on Patentability, dated Oct. 29, 2013.
PCT/US2012/034333, International Search Report, dated Aug. 29, 2013.
U.S. Appl. No. 13/424,429.
U.S. Appl. No. 13/424,479.
U.S. Appl. No. 13/424,525.
U.S. Appl. No. 61/480,528.
U.S. Appl. No. 61/480,530.
U.S. Appl. No. 61/480,535.
U.S. Appl. No. 61/480,539.
U.S. Appl. No. 61/480,541.
Weiner, et. al., Article: Cardiac Function and Cardiovascular Disease in Chronic Kidney Disease, Book: Primer on Kidney Diseases (Author: Greenberg, et al), 2009,499-505, 5th Ed., Saunders Elsevier, Philadelphia, PA.
Bleyer, et. al., Sudden and cardiac death rated in hemodialysis patients, Kidney International. 1999, 1553-1559: 55.
EP 14746799 Supplementary European Seach Report dated Aug. 18, 2016.
EP13182115.9-1651 European Search Report, dated Feb. 3, 2014.
International Search Report for PCT/US2015/060090 dated Feb. 9, 2016 (3 pages).
Ruperez et al., Comparison of a tubular pulsatile pump and a volumetric pump for continuous venovenous renal replacement therapy in a pediatric animal model, 51 ASAIO J. 372, 372-375 (2005).
St. Peter et al., Liver and Kidney Preservation by perfusion, 369 The Lancet 604, 606 (2002).
Dasselaar et al., Measurement of relative blood volume changes during hemodialysis: merits and limitations, 20 Nephrol Dial Transpl. 2043, 2043-2044 (2005).
Ralph T. Yang, Adsorbents: Fundamentals and Applications 109 (2003).
Henny H. Billett, Hemoglobin and Hematocrit, in Clinical Methods: The History, Physical, and Laboratory Examinations 719(HK Walker, WD Hall, & JW Hurst ed., 1990).
Franks, Gene, Cabon Filtration: What it does, What it doesn't, Mar. 14, 2012, pp. 1-3.
EP Search Report for Application No. 16204175.0 dated Mar. 29, 2017.
Office Action for Chinese Application 201510713880.1 dated Apr. 1, 2017.
EP Search report for Application No. 15193645.7, dated Apr. 15, 2016.
EP Office Action for Application No. 15193645.7, dated Apr. 21, 2017.
Examination report for Australian Application No. AU2014212135 dated May 25, 2017.
Office Action for Chinese Application 201510761050.6 dated Aug. 2, 2017.
Examination report for Australian Application 2015361083 dated Jul. 20, 2017.
European Search Report and Search Opinion for European Application EP15193720 dated May 2, 2016.
Office Action in European Application No. 15193720.8 dated Apr. 25, 2017.
Written Opinion for PCT/US2015/060090 dated Feb. 16, 2016.
International Preliminary Report on Patentability for PCT2015/060090 dated Jun. 13, 2017.
European Search Report for European Application EP 15193830.5 dated May 4, 2016.
Office Action for European Application No. 15193645.7 dated Apr. 21, 2017.
Office Action for Chinese Application 20148007136.3, dated Jun. 15, 2017.
European Office Action in Application 14746793.0 dated Apr. 13, 2017.

\* cited by examiner

WATER MANAGEMENT SYSTEM FOR USE IN DIALYSIS

FIELD OF THE INVENTION

The invention relates to a water management system for use in sorbent dialysis. The water management system allows for the creation, storage, and use of purified water for rinsing, cleaning and disinfection in dialysis system and related processes.

BACKGROUND

Sorbent-based regenerative hemodialysis systems can provide benefits such as the ability to provide hemodialysis treatments with a reduced volume of source water and without the requirement to receive the source water from water purification systems that are commonly used to filter and purify the dialysate for hemodialysis treatments. Some sorbent-based regenerative hemodialysis systems can provide a hemodialysis treatment using a smaller quantity of potable water than traditional single-pass hemodialysis systems. Purified water can be difficult to obtain in many locations through-out the world. Eliminating the need to provide fresh purified water for each dialysis session can enable patients in such areas to obtain necessary treatment.

Microbiologically ultrapure dialysate is desirable for hemodialysis treatment. Ultrapure dialysate is defined as dialysate having less than 0.1 colony forming units per milliliter and less than 0.03 endotoxin units per milliliter. Microbial filters, such as ultra-filters, can be used to remove microorganisms and other unwanted substances such as endotoxins from water used to prepare dialysate, or from the dialysate itself, before the dialysate enters the dialyzer in order to prevent their transfer to the patient during hemodialysis. To minimize the cost of providing hemodialysis treatment, using non-disposable dialysate flow path components, and multi-use ultra-filters that can be used for more than a single treatment session is often desirable. Non-disposable dialysate flow paths must also be routinely cleaned and disinfected to prevent microbial growth and formation of bio-film so that viable microorganisms and remnants of dead microorganisms, such as endotoxins, are minimized.

Sorbent-based regenerative hemodialysis systems can purify potable water to produce dialysate for hemodialysis treatment. In addition to chemical purification, sorbents can be designed to remove microbiological and particulate contaminants that may also exist in potable water. An ultra-filter can be added to the dialysate preparation flow path between the sorbent outlet and the dialyzer inlet to remove remaining microorganisms and endotoxin from the dialysate to ensure that a microbiologically ultrapure dialysate is produced. To achieve a long, economically efficient ultra-filter service life, removal of particulate matter that could clog the fine pores of an ultra-filter from the liquid by the sorbent before the liquid passes through the ultra-filter is important.

The sorbents may be removed from the dialysate flow path of sorbent-based regenerative hemodialysis system during rinsing, cleaning and disinfection of the dialysate flow path. However, if the sorbents are not present in the flow path to remove chemical contaminants, microorganisms, and fine particulate matter contained in the incoming source water, then the dialysate flow path may be contaminated and may require alternate cleaning processes. Further, the fine pores of the ultra-filter may become clogged, rendering the ultra-filter unusable after only a brief service life.

Hence, there is a need for a system whereby purified water can be generated and stored within the dialysis system for later cleaning and disinfection, thereby eliminating the need for attaching an external source of purified water after each dialysis session. There is also a need for a system allowing for a single-time connection of the rinse water reservoir to the rest of the dialysis system, thus simplifying the cleaning and disinfection process.

SUMMARY OF THE INVENTION

The first aspect of the invention is directed to a water management system for use in sorbent dialysis. In any embodiment of the first aspect of the invention, the water management system can comprise a rinse water reservoir configured to receive water obtained from a sorbent cartridge wherein the rinse water reservoir is fluidly connectable to one or more valves in a dialysate circuit defining a fluid flow path; wherein the one or more valves are fluidly connectable to a water source and the sorbent cartridge; and the water management system can comprise a drain wherein the drain is fluidly connectable to one or more valves; wherein the one or more valves are fluidly connectable to a dialysis circuit.

In any embodiment of the first aspect of the invention, the water source can be a water reservoir.

In any embodiment of the first aspect of the invention, the drain can comprise a waste reservoir.

In any embodiment of the first aspect of the invention, the water management system can be part of a controlled compliant dialysis circuit. In any embodiment of the first aspect of the invention, the water management system can be part of a controlled volume dialysis circuit.

In any embodiment of the first aspect of the invention, the water management system can further comprise a microbial filter positioned in a fluid flow path after the sorbent cartridge and before a dialyzer, wherein the microbial filter is fluidly connectable to the rinse water reservoir.

In any embodiment of the first aspect of the invention, the water management system can further comprise one or more pumps to direct the fluid in the fluid flow path.

In any embodiment of the first aspect of the invention, the water management system can further comprise a programmable controller to control the pumps and valves.

Any of the features disclosed as being part of the first aspect of the invention can be included in the first aspect of the invention, either alone or in combination.

The second aspect of the invention directed to a method of filling a rinse water reservoir of a water management system. In any embodiment of the second aspect of the invention, the method can comprise the step of directing water from a water source, through a sorbent cartridge, and then into the rinse water reservoir.

In any embodiment of the second aspect of the invention, the method can comprise directing water through a microbial filter prior to the step of directing water into the rinse water reservoir.

In any embodiment of the second aspect of the invention, the water from the water source can travel through a dialysate circuit defining a fluid flow path before flowing into the rinse water reservoir.

In any embodiment of the second aspect of the invention, the method can comprise the step of directing water from the water source through the lines of the dialysis system and into a drain prior to the step of directing water from the water source through the sorbent cartridge and into the rinse water reservoir.

In any embodiment of the second aspect of the invention, the method can further comprise the step of blowing out the lines of the dialysis system with air prior to directing water from the water source through the lines of the system.

In any embodiment of the second aspect of the invention, the step of directing water from the water source through the lines of the dialysis system and into a water source can be repeated multiple times prior to directing water into the rinse water reservoir.

In any embodiment of the second aspect of the invention, the step of directing water from the water source through the lines of the dialysis system and into a drain can continue until a predetermined volume of water has been flushed through the dialysate flow path prior to directing water into the rinse water reservoir.

In any embodiment of the second aspect of the invention, the step of directing water from the water source through the lines of the dialysis system and into a drain can be repeated a pre-set number of times.

In any embodiment of the second aspect of the invention, the step of directing water from the water source through the lines of the dialysis system and into a drain can be repeated any of 2, 3, 4, 5, 6, or more times.

In any embodiment of the second aspect of the invention, the method can further comprise the step of taking a conductivity measurement after directing water from the water source through the lines of the dialysis system and into a drain, and the step of directing water from the water source through the lines of the dialysis system and into a drain can be repeated until the conductivity measurement shows a conductivity below a pre-set number.

In any embodiment of the second aspect of the invention, the method can include using a programmable controller to operate one or more valves and one or more pumps to direct the filling of the rinse water reservoir.

In any embodiment of the second aspect of the invention, the waste reservoir can be replaced by a connection to a plumbing waste or drain line.

Any of the features disclosed as being part of the second aspect of the invention can be included in the second aspect of the invention, either alone or in combination.

The third aspect of the invention is drawn to a method of disinfecting a dialysis system. In any embodiment of the third aspect of the invention, the method can comprise directing purified water from a rinse water reservoir through the lines of the dialysis system wherein the purified water has passed through a sorbent cartridge prior to addition to the rinse water reservoir. In any embodiment of the third aspect of the invention, the method can comprise circulating heated water through the system.

In any embodiment of the third aspect of the invention, the method can further comprise the steps of attaching a citric acid cartridge to the dialysis system, directing water from the rinse water reservoir through the citric acid cartridge to create a citric acid solution, and heating the citric acid solution while circulating the citric acid solution through the lines of the system.

In any embodiment of the third aspect of the invention, the system can be heated to a temperature between any of 60-100° C., 65-75° C., 65-90° C., 75-85° C. or 85-100° C. while circulating the fluid.

In any embodiment of the third aspect of the invention, the method can further comprise the step of blowing out the lines of the dialysis system with air prior to directing water from the rinse water reservoir through the lines of the system.

In any embodiment of the third aspect of the invention, the citric acid cartridge can contain dry citric acid.

In any embodiment of the third aspect of the invention, the citric acid cartridge can contain a predetermined amount of citric acid, and the method can comprise the step of dissolving the citric acid with the water directed through the citric acid cartridge to create a citric acid solution of a predetermined concentration.

Any of the features disclosed as being part of the third aspect of the invention can be included in the third aspect of the invention, either alone or in combination.

DETAILED DESCRIPTION OF THE INVENTION

Figure 1:
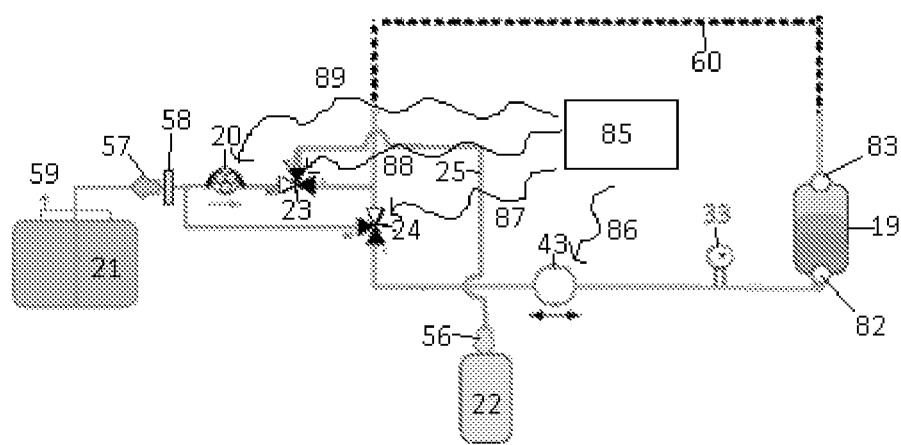
FIG. 1 shows a schematic of a rinse water reservoir and water source reservoir in accordance with any embodiment of the invention.

Unless defined otherwise, all technical and scientific terms used herein generally have the same meaning as commonly understood by one of ordinary skill in the relevant art.

The articles "a" and "an" are used herein to refer to one or to more than one (i.e., to at least one) of the grammatical object of the article. By way of example, "an element" means one element or more than one element.

"Bypass line" refers to a line, connected to the main line, through which fluid or gas may alternatively flow.

The term "cartridge" refers to any container designed to contain a powder, fluid, or gas made for ready connection to a device or mechanism. The container can have one or more compartments. Instead of compartments, the container can also be comprised of a system of two or more modules connected together to form the cartridge wherein the two or more modules once formed can be connected to a device or mechanism.

The term "cation infusate source" refers to a source from which cations can be obtained. Examples of cations include, but are not limited to, calcium, magnesium and potassium. The source can be a solution containing cations or a dry composition that is hydrated by the system. The cation infusate source is not limited to cations and may optionally include other substances to be infused into a dialysate or replacement fluid; non-limiting examples can include glucose, dextrose, acetic acid and citric acid.

The term "comprising" includes, but is not limited to, whatever follows the word "comprising." Thus, use of the term indicates that the listed elements are required or mandatory but that other elements are optional and may or may not be present.

A "connector" and "for connection" as used herein describes forming a fluid connection between two components wherein fluid or gas can flow from one component, through a connector or a component for connection, to another component. The connector provides for a fluid connection in its broadest sense and can include any type of tubing, fluid or gas passageway, or conduit between any one or more components of the invention.

The term "consisting of" includes and is limited to whatever follows the phrase "consisting of." Thus, the phrase indicates that the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "container" as used herein in the context of a controlled compliant circuit or controlled volume circuit is a receptacle that may be flexible or inflexible for holding any fluid or solid, such as for example a spent dialysate fluid, or a sodium chloride or sodium bicarbonate solution or solid, or the like.

A "control system" consists of combinations of components that act together to maintain a system to a desired set of performance specifications. The control system can use processors, memory and computer components configured to interoperate to maintain the desired performance specifications. The control system can also include fluid or gas control components, and solute control components as known within the art to maintain the performance specifications.

The term "controlled volume" refers to a flow path, fluid circuit, or system wherein a volume of fluid in the flow path, flow circuit, or system, exclusive of any volume of fluid contained in an external reservoir, supply line, or fluid removal line, is substantially fixed. In any embodiment, a controlled volume flow path is not fluidly connected to, nor includes, an open reservoir or a reservoir having a variable volume, such as a reservoir made of a flexible material.

A "controller," "control unit," "processor," or "microprocessor" is a device which monitors and affects the operational conditions of a given system. The operational conditions are typically referred to as output variables of the system wherein the output variables can be affected by adjusting certain input variables.

A "degasser" is a component that is capable of removing dissolved and undissolved gasses from fluids. The term "degasser" can encompass a degassing vessel, and a fluid pump and a vacuum pump connected to the degassing vessel and working in concert to create a vacuum in the fluid flowing through the degassing vessel and to evacuate gas from the degassing vessel.

The term "detachable" or "detached" relates to any component of the present invention that can be separated from a system, module, cartridge or any component of the invention. "Detachable" can also refer to a component that can be taken out of a larger system with minimal time or effort. In certain instances, the components can be detached with minimal time or effort, but in other instances can require additional effort. The detached component can be optionally reattached to the system, module, cartridge or other component. A detachable module can often be part of a reusable module.

"Dialysate" is the fluid that passes through the dialyzer on the side of the dialysis membrane that is opposite to the fluid (e.g. blood) that is being dialyzed.

"Dialysis" is a type of filtration, or a process of selective diffusion through a membrane. Dialysis removes solutes of a specific range of molecular weights via diffusion through a membrane from a fluid to be dialyzed into a dialysate. During dialysis, a fluid to be dialyzed is passed over a filter membrane, while dialysate is passed over the other side of that membrane. Dissolved solutes are transported across the filter membrane by diffusion between the fluids. The dialysate is used to remove solutes from the fluid to be dialyzed. The dialysate can also provide enrichment to the other fluid.

The term "dialyzer" refers to a cartridge or container with two flow paths separated by semi-permeable membranes. One flow path is for blood and one flow path is for dialysate. The membranes can be in the form of hollow fibers, flat sheets, or spiral wound or other conventional forms known to those of skill in the art. Membranes can be selected from the following materials of polysulfone, polyethersulfone, poly(methyl methacrylate), modified cellulose, or other materials known to those skilled in the art.

A "drain" is any conduit, connector, reservoir, or container that is designed or used to hold or transport fluid, or combinations thereof. "Flow" refers to the movement of a fluid or gas.

A "flow sensing apparatus" or "flow measuring apparatus" is an apparatus capable of measuring the flow of fluid or gas within a specific area.

A "fluid" is a liquid substance optionally having a combination of gas and liquid phases in the fluid. Notably, a liquid, as used herein, can therefore also have a mixture of gas and liquid phases of matter.

The term "fluid communication" refers to the ability of fluid or gas to move from one component or compartment to another within a system or the state of being connected, such that fluid or gas can move by pressure differences from one portion that is connected to another portion.

The terms "fluidly connectable" and "fluid connection" refer to the ability of providing for the passage of fluid or gas from one point to another point. The two points can be within or between any one or more of compartments, modules, systems, components, and rechargers, all of any type.

"Infusate" is a solution of one or more salts for the adjustment of the composition of a dialysate.

An "operational line" or "line" is a passageway, conduit or connector that directs fluid or gas in a path used while the system is in operation.

The terms "pathway," "conveyance pathway," "fluid flow path," and "flow path" refer to the route through which a fluid or gas, such as dialysate or blood travels.

The terms "pressure meter" and "pressure sensor" refer to a device for measuring the pressure of a gas or fluid in a vessel or container.

The term "pump" refers to any device that causes the movement of fluids or gases by the application of suction or pressure.

"Purified water" is water that has been passed through at least a sorbent cartridge. In any embodiment, purified water can refer to water that has undergone additional purification, such as by passing the water through any one of a microbial filter, an ultrafilter, any other cleaning apparatus, and combinations thereof. Purified water is water that can be sufficiently free from chemical and microbiological contamination so that the purified water can serve the intended purpose for a function of the hemodialysis system.

A "rinse water reservoir" is a container for storing purified water in a dialysis system for later use in rinsing, cleaning, or disinfection of the dialysate circuit, or for use in dialysis.

A "sensor" is a component capable of determining the states of one or more variables in a system.

"Sorbent cartridge" refers to a cartridge that can contain one or more sorbent materials. The cartridge can be connected to a dialysis flow path. The sorbent materials in the sorbent cartridge are used for removing specific solutes from solution, such as urea. The sorbent cartridge can have a single compartmental design wherein all sorbent materials necessary for performing dialysis are contained within the single compartment. Alternatively, the sorbent cartridge can have a modular design wherein the sorbent materials are dispersed across at least two different modules, which can be connected to form a unitary body. Once the at least two modules are connected together, the connected modules can be referred to as a sorbent cartridge, which can be fitted to a device or mechanism. It will be understood that when a single module contains all the sorbent materials necessary for performing dialysis, the single module can be referred to as a sorbent cartridge.

"Source water" is water that is supplied to the system as a fluid source for operation of the system.

A "source water reservoir" is a container designed to hold water that can be used during a dialysis session.

"Spent dialysate" is a dialysate contacted with blood through a dialysis membrane and contains one or more impurity, or waste species, or waste substance, such as urea.

"Tap water" refers to water obtained through piping from a water supply without additional treatment.

An "ultrafiltrate container" is a container designed to receive and store in part fluid removed from a dialysis system by ultrafiltration.

A "valve" is a device capable of directing the flow of fluid or gas by opening, closing or obstructing one or more pathways to allow the fluid or gas to travel in a particular path. One or more valves configured to accomplish a desired flow can be configured into a "valve assembly."

The term "waste fluid" refers to any fluid that does not have a present use in the operation of the system. Non-limiting examples of waste fluids include ultrafiltrate, or fluid volume that has been removed from a subject undergoing a treatment, and fluids that are drained or flushed from a reservoir, conduit or component of the system.

A "waste reservoir" is a container designed to hold waste fluids.

The term "water source" refers to a source from which potable or not potable water can be obtained.

Water Management System

Commonly, a dialysate circuit will be filled with a citric acid solution, or some other disinfectant, after dialysis is complete in order to clean and disinfect the dialysate circuit. Before starting a new dialysis session, the citric acid must be flushed, and the system filled and primed with water in order to ensure that the disinfectant is sufficiently removed from the dialysate circuit before starting a new dialysis session. In any embodiment of the first, second and third aspects of the invention this flushing step may be achieved using water from a rinse water reservoir. In any embodiment of the first, second and third aspects of the invention, the flushing can be accomplished with water from a water source other than the rinse water reservoir, such as with tap water.

The rinse water reservoir and accompanying portions of a non-limiting embodiment of a dialysate circuit of the first, second and third aspects of the invention are shown in FIG. 1. A rinse water reservoir 22 can be fluidly connectable to a dialysate circuit 60. In order to fill the rinse water reservoir 22 with purified water, water from source water reservoir 21 can be directed into the dialysate circuit 60 through the operation of fast fill valve 24 and dialysate pump 43. Pump 20 can optionally be used to initially prime the flow path 60 and can be controlled by control system 85 through signal 89. In any embodiment of the first, second or third aspects of the invention, the fast fill valve 24 can be controlled by control system 85 through signal 87. Dialysate pump 43 can be controlled by the control system 85 through signal 86. Vent 59 can allow air to enter the source water reservoir 21 as water is removed from the source water reservoir 21. The pressure of water entering the sorbent cartridge 19 can be measured by sorbent pressure sensor 33. The water from source water reservoir 21 can travel through source water reservoir connector 57 and water filter 58 in order to remove gross particulate matter from the water. By opening fast fill valve 24, which can be controlled by control system 85 through signal 87, to source water reservoir 21 and closing reverse drain valve 23, which can be controlled by control system 85 through signal 88, to rinse water reservoir 22, the water from source water reservoir 21 can be directed to sorbent cartridge 19 by dialysate pump 43. The water enters the sorbent cartridge 19 through inlet sorbent cartridge connector 82 and exits through outlet sorbent cartridge connector 83. The water can be purified by the sorbent cartridge 19 and then travel through the rest of the dialysate circuit, represented by dotted line 60. The sorbent cartridge 19 can remove chemical contaminates, microbial contaminants and particulate material from the water as the water passes through the sorbent cartridge 19. The water obtained after passing through the sorbent cartridge 19 can be flowed to the rinse water reservoir 22. Fast fill valve 24 and reverse drain valve 23 can be set so that the now purified water from the sorbent cartridge 19 is directed into rinse water reservoir line 25. The purified water can then travels through rinse water reservoir connector 56 and into the rinse water reservoir 22. The purified water can be stored in rinse water reservoir 22 until needed for rinsing, cleaning or disinfection. The signals from the control system 85 to the pumps and valves can be conducted wirelessly, or through wired communication. In any embodiment of the first, second and third aspects of the invention, the initial water source can be an external source, such as tap water from a tap, as opposed to the source water reservoir 21. In any embodiment of the first, second or third aspects of the invention, the dialysate circuit 60 can have a controlled volume. In any embodiment of the first, second or third aspects of the invention, the dialysate circuit 60 can have a controlled compliance. In any embodiment of the first, second and third aspects of the invention, the purified water can also be passed through an ultrafilter prior to being added to the rinse water reservoir 22.

Figure 2:
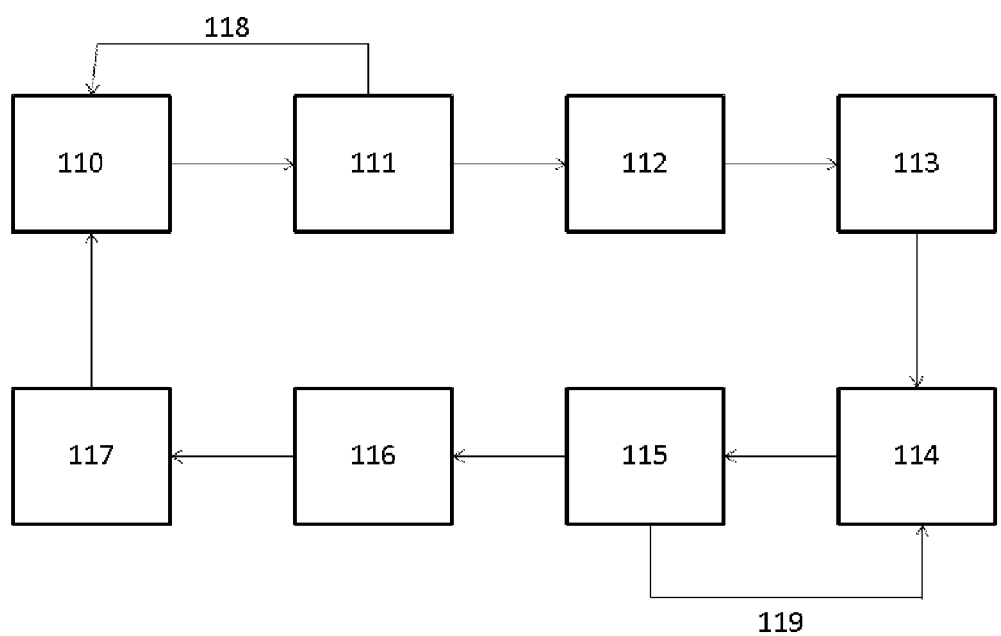
FIG. 2 shows a flow diagram of the steps necessary to fill, use, clean and disinfect a dialysis system in accordance with any embodiment of this invention.

The process for using the water management system of the first, second and third aspects of the invention is shown in FIG. 2. Each of the steps depicted is described in more detail herein. Before a dialysis session can begin, the system can be drained of the disinfection solution initially present 110. Next, the system is flushed with water from the source water reservoir 111. The water used in the flushing step 111 has been purified by passing through the sorbent cartridge as explained herein. In any embodiment of the first, second and third aspects of the invention, the draining step 110 is optional and need not be a separate step in the process. Instead, the disinfection solution can be removed during the flushing step 111. In any embodiment of the first, second and third aspects of the invention where the draining step 110 is omitted, the flushing step can be completed while the system is open to the drain or waste reservoir as shown in FIG. 1. In any embodiment of the first, second and third aspects of the invention, the drain can be a plumbing drain connection, or a waste reservoir. The water from the source water reservoir can be added to the system, pushing the disinfection solution originally present into the drain. Removing the disinfection solution during flushing instead of draining the disinfection solution can result in an increased amount of water necessary to ensure that the traces of the disinfection solution are sufficiently removed prior to priming of the system 112. The flushing and optionally draining processes can be repeated multiple times, as shown by arrow 118. After the draining and flushing process is finished, the system can be primed and the rinse water reservoir can be filled with purified water 112, wherein the water has passed through the sorbent cartridge as explained herein with reference to FIG. 1. A dialysis treatment session can then begin 113. After treatment is complete, the system can again be drained 114. The system can be flushed 115 with purified water from the rinse water reservoir to remove salts and impurities that may be left as residues in the system, by directing purified water from the rinse water reservoir through the lines of the dialysis system as explained herein. This draining and flushing process can be repeated multiple times to ensure that the salts and impurities are sufficiently removed, as shown by arrow 119. The draining step 114 can be optional in any embodiment of the first, second and third aspects of the invention. Instead, the water can be removed during the flushing step 115. After the flushing of the system is complete, the system can be filled with purified water from the rinse water reservoir 116. The system can then be disinfected 117. After the disinfection process 117, the process can be repeated for the next patient.

Figure 3:
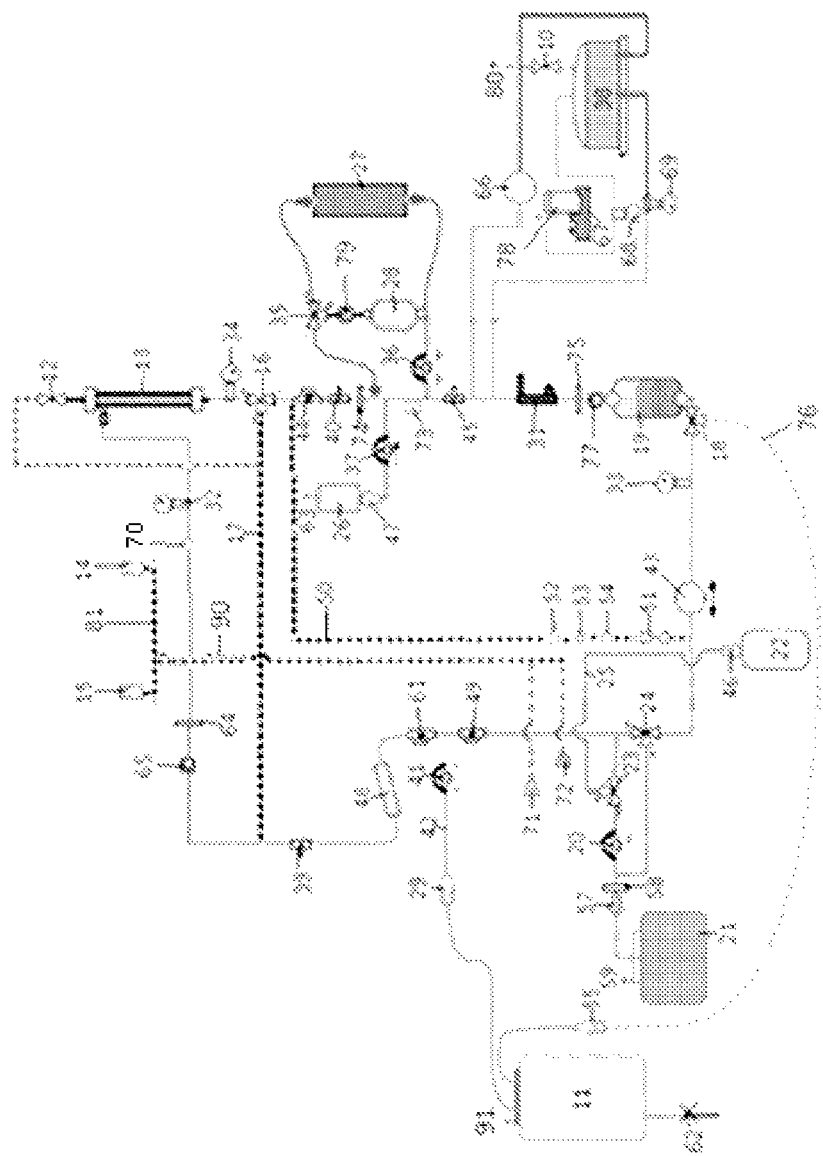
FIG. 3 shows a schematic of a dialysate circuit including a water management system in accordance with any embodiment of this invention.

One non-limiting embodiment of a dialysate circuit with a water management system of the first, second and third aspects of the invention is shown in FIG. 3. Commonly, the dialysate circuit will be filled with a citric acid solution after dialysis is complete for purposes of cleaning and disinfection. Before starting a new dialysis session, the citric acid must be flushed, and the system filled and primed with water. Flushing and priming the system with water ensures that the initial dialysate is sufficiently free of residual citric acid or other impurities that may remain from the cleaning process. The citric acid may be drained by blowing air to enter at vent valve 10 while valve 18 is open to waste reservoir 11, to direct the citric acid solution through the drain line 76 and into the waste reservoir 11 through waste reservoir connector 55. In any embodiment of the first, second and third aspects of the invention, the waste reservoir 11 may also serve as an ultrafiltrate reservoir. In any embodiment of the first, second and third aspects of the invention, a separate ultrafiltrate reservoir can be provided (not shown). The waste reservoir 11 can have clamp 62, or a valve, which can be opened in order to move waste fluid from the waste reservoir 11 to a transport container or the actual drain (not shown). The air drawn in through vent valve 10 will allow the fluid in the dialysate circuit to enter waste reservoir 11, without creating an excessive vacuum in the fluid circuit. By opening microbial filter valve 12, the fluid in the microbial filter 13 can be drained. If microbial filter valve 12 is closed, the fluid will be drained out of that portion of jumper line 90 between the dialyzer connectors 14 and 15. By controlling dialyzer by-pass valve 16, the solution can be drained from the dialyzer by-pass line 17 and flush the fluid from the dialyzer by-pass line 17. Ultrafiltrate pump 41 can also be utilized to flush the fluid from ultrafiltrate line 42. The fluid can thus be drained from all of the lines of the dialysate circuit into the waste reservoir 11. The fast drain valve 18 can be controlled to direct fluid into the waste reservoir 11 prior to the fluid reaching the sorbent cartridge 19. Although less flushing water can be consumed if the citric acid solution is first drained by the preceding sequence, the draining step is optional, and the fluid can be removed during the flushing step as explained herein.

In any embodiment of the first, second and third aspects of the invention the waste reservoir 11 can also serve as an ultrafiltrate reservoir. In any embodiment of the first, second and third aspects of the invention, a separate ultrafiltrate reservoir can be provided to contain fluid removed by ultrafiltration. In any embodiment of the first, second and third aspects of the invention with a separate ultrafiltrate reservoir, the fluid removed from the ultrafiltrate reservoir can be reused in the dialysate circuit, particularly in home environments or when the system is specific to a single patient in order to avoid contamination between patients. Reusing the fluid in the ultrafiltrate reservoir allows for further reduction of fluid requirements. In any embodiment of the first, second and third aspects of the invention wherein the waste reservoir 11 also serves as the ultrafiltrate reservoir, the fluid can be reused for any purposes including dialysis, hemodialysis, hemodiafiltration, or peritoneal dialysis, if the fluid is cleaned or processed prior to reuse. Such re-use of cleaned fluid, whether mixed or not with waster fluid can be particularly useful in home dialysis settings.

Once the citric acid solution has been removed from the dialysate circuit, the dialysate circuit must be flushed with water in order to remove remaining solutes. Utilizing water pump 20, and dialysate pump 43, water can be directed from source water reservoir 21 to flush the dialysate circuit. The lines of the dialysate circuit positioned before the sorbent cartridge 19 can be flushed by controlling fast drain valve 18 to direct fluid into the waste reservoir 11 prior to reaching the sorbent cartridge 19. The sorbent cartridge 19 can then be primed with water by switching fast drain valve 18 so that the water from source water reservoir 21 can enter the sorbent cartridge 19. Water can be pumped into the system by action of the dialysate pump 43 if valve 24 is controlled to draw water from source water reservoir 21. Sorbent cartridge check valve 77 serves to ensure that no fluid enters the sorbent cartridge 19 from the opposite direction. Adding water to the sorbent cartridge 19 will push out any air within the sorbent cartridge 19. The air can travel through degas vessel 38 to vent valve 10 and leave the system, as represented by arrow 80. Using a pressure gauge, such as dialysate pressure inlet sensor 32, the system can determine when the sorbent cartridge 19 is full. Once the sorbent cartridge 19 is primed with water, the rest of the dialysate circuit can be filled with water in the same manner. Water from source water reservoir 21 can pass through the sorbent cartridge 19 and into the rest of the dialysate circuit. Sorbent filter 75 can filter out any particles contained in the fluid exiting the sorbent cartridge 19. In this way, the entire dialysate circuit can be filled with water from the source water reservoir 21. The microbial filter 13 can be filled by opening dialyzer bypass valve 16 and microbial filter valve 12, allowing water to pass from the sorbent cartridge 19 through the microbial filter 13. The degassing vessel 38, degassing pump 66 and the associated lines can be filled by drawing fluid into the degassing vessel 38 with degassing pump 66. During the filling process, air can leave the system through degas vessel 38 and vent valve 10, and waste water can be collected into waste reservoir 11. In any embodiment of the first, second and third aspects of the invention, the draining and flushing steps may be repeated multiple times to ensure that the citric acid residue present in the dialysate circuit is sufficiently removed. In any embodiment of the first, second and third aspects of the invention, the draining and flushing steps may be repeated a pre-determined number of times. The draining and flushing steps can be repeated 2, 3, 4, 5, 6 or more times. In any embodiment of the first, second and third aspects of the invention, the maximum amount of water that will be moved to the waste reservoir 11 is 1 L. In any embodiment of the first, second and third aspects of the invention, between 0.5-5.0 L, 0.5-1.5 L, 1.0-2.0 L, 1.5-3.0 L or 2.5-5.0 L of water may be moved to the waste reservoir.

Once the system is properly flushed and primed, the rinse water reservoir 22 can be filled with purified water for later use in cleaning and disinfection. Water from the source water reservoir 21 can be directed through the dialysate circuit, including sorbent cartridge 19, and optionally microbial filter 13, before being directed into the rinse water reservoir 22 by controlling the reverse drain valve 23 and fast fill valve 24. Directing the water through microbial filter 13 before the water enters the rinse water reservoir 22 can allow for the removal of microbiological contamination that may be in the water. The fast fill valve 24 can be set to direct water from the source water reservoir 21 through the dialysate circuit by opening the fast fill valve 24 to the source water reservoir and to the dialysate circuit lines. The reverse drain valve 23 can be set so that water returning from the dialysate circuit is directed through the rinse water reservoir line 25 and through rinse water reservoir connector 46. During the filling of the rinse water reservoir 22, air can be removed from the fluid by using degassing pump 66 to draw the water into the degassing vessel 38, where dissolved and undissolved gases can be captured in degassing chamber 38 and removed by gas removal pump 78 on gas removal apparatus 67.

Flow of water throughout the system of the first, second and third aspects of the invention can be detected by inlet flow sensor 44 and outlet flow sensor 61 and outlet flow sensor 49. Inlet flow sensor 44 and outlet flow sensor 61 can be utilized to determine the amount of purified water that is moved to rinse water reservoir 22. In any embodiment of the first, second and third aspects of the invention, the purified water contained in the rinse water reservoir 22 can be sufficient to both flush the dialysate fluid circuit after a treatment has been delivered and to create a solution for a cleaning and disinfection process. In any embodiment of the first, second and third aspects of the invention, 1.5 L of water can be moved to fill the rinse water reservoir 22. In any embodiment of the first, second and third aspects of the invention, less than 1 L of water may be necessary to fill the rinse water reservoir 22.

The rinse water reservoir 22 can be constructed of any material known in the art. In any embodiment of the first, second and third aspects of the invention, the rinse water reservoir 22 can be constructed out of plastic. In any embodiment of the first, second and third aspects of the invention, the rinse water reservoir 22 can be constructed out of metal. In any embodiment of the first, second and third aspects of the invention, the rinse water reservoir 22 can be made of a flexible material, such as a bag. The rinse water reservoir 22 is ideally of a large enough size to contain enough purified water to complete the flushing and disinfection process described below. In any embodiment of the first, second and third aspects of the invention, the rinse water reservoir 22 can have a capacity between 0.5 L and 2.5 L. In any embodiment of the first, second and third aspects of the invention, the rinse water reservoir 22 can have a capacity between any of 0.5 L to 1.5 L, 1.5 L to 2.5 L, 2.0 L to 2.5 L, or more.

Figure 4:
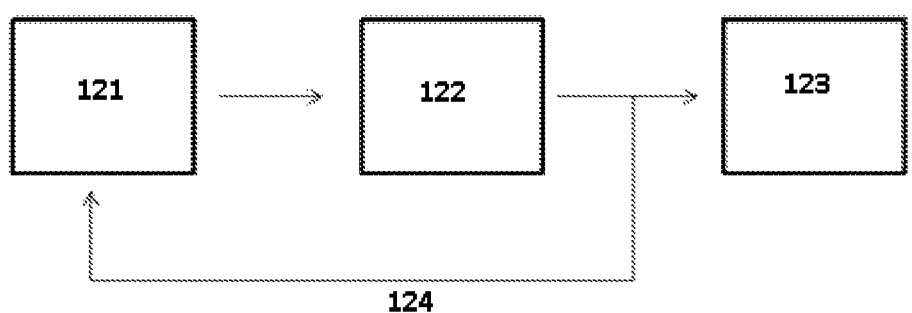
FIG. 4 is a flow diagram showing the method of filling a rinse water reservoir with purified water.

FIG. 4 shows a flow chart illustrating the process of filling the rinse water reservoir 22 (shown in FIG. 3) with purified water. The first step, represented by box 121, is draining the dialysate circuit of fluid. As explained herein, step 121 is optional in any embodiment of the first, second and third aspects of the invention. Once the dialysate circuit is drained, step 122 rinses the dialysate circuit with water from the source water reservoir that has been purified by passing through a sorbent cartridge as explained herein. In any embodiment of the first, second and third aspects of the invention, the steps of draining the dialysate circuit 121 and rinsing the dialysate circuit 122 with water that has been first purified by passing through sorbent cartridge can be repeated, as shown by arrow 124. In any embodiment of the first, second and third aspects of the invention, the steps of draining the dialysate circuit 121 and rinsing the dialysate circuit 122 can be repeated a pre-set number of times. In any embodiment of the first, second and third aspects of the invention, the steps of draining the dialysate circuit 121 and rinsing the dialysate circuit 122 can be repeated 2, 3, 4, 5, 6 or more times. In any embodiment of the first, second and third aspects of the invention, the draining step 121 is optional, and the flushing step 122 can be continued until a predetermined volume of water has flushed through the system. In any embodiment of the first, second and third aspects of the invention, the purity of the water in the dialysate circuit after the rinsing can be determined by taking conductivity measurements. If the conductivity measurements are too high, showing that the water in the dialysate circuit is not sufficiently clean, then the rinsing can be repeated until the conductivity measurements show that the water is sufficiently free of impurities. Once the dialysate circuit is properly rinsed, the rinse water reservoir can be filled with purified water 123, by directing fluid from the source water reservoir 21, through the sorbent cartridge 19, and into the rinse water reservoir 22 as shown in FIG. 3.

Again referring to FIG. 3, the water flowing through the sorbent cartridge 19 and into the rinse water reservoir 22 is not salted prior to filling the rinse water reservoir 22 so that the water in the rinse water reservoir 22 remains sufficiently pure. After the rinse water reservoir is filled, the dialysate circuit and lines must be salted to prime the dialysate circuit with a physiologically compatible solution. This can be accomplished by first priming the sodium chloride reservoir 28 with water from the source water reservoir 21. Water can be directed into the sodium chloride reservoir 28 by controlling sodium chloride valve 35 so that the valve 35 is open to the sodium chloride reservoir 28 and using cartridge pump 36 to draw water into the sodium chloride reservoir 28. Water is kept from flowing into the sodium chloride reservoir 28 during the draining and flushing processes by sodium chloride reservoir check valve 79. Cation infusate source 26 is a source of cations that can be added to regenerated dialysate by action of infusate pump 37. The cation infusate source 26 is fluidly connected to infusate pump 37 by infusate pump connector 47. In any embodiment of the first second and third aspects of the invention, cation infusate source 26 can be constructed of rigid material wherein a gas such as air can be drawn into the cation infusate source 26 through vent 63, as the infusate is metered out by action of pump 37. The bicarbonate reservoir 27 can be primed by switching sodium chloride valve 35 so that the valve 35 is instead open to the bicarbonate reservoir 27. Once the reservoirs are primed, the dialysate circuit can be filled with a physiologically compatible solution by circulating water through the sodium chloride reservoir 28 and then through all of the lines of the dialysate circuit, including the microbial filter 13. The concentration of sodium chloride and bicarbonate in the dialysate circuit during the priming steps can be detected by conductivity sensors 39, 40, and 45.

The microbial filter 13 can be salted by opening dialyzer bypass valve 16 and microbial filter valve 12 to allow salted fluid to enter the microbial filter 13. The dialyzer bypass line 17 can be salted by switching dialyzer bypass valve 16 to direct fluid into the dialyzer bypass line 17. The dialyzer loop 81 can be salted by closing microbial filter valve 12 and switching dialyzer bypass valve 16 to direct fluid through the jumper line 90 between dialyzer connectors 14 and 15. After salting all of the lines of the dialysate circuit the dialyzer connectors 14 and 15 can be removed from jumper line 90 and connected to the dialyzer (not shown) to complete priming of the dialyzer (not shown).

During dialysis treatment, spent dialysate is recirculated through the dialysate circuit and regenerated. A dialyzer (not shown) will be placed between dialyzer connectors 14 and 15. Prior to reaching the dialyzer, the dialysate will travel past particulate filter 74, which serves to trap any larger particulates that may have been introduced from the dry salts contained in sodium chloride container 28 or sodium bicarbonate container 27. After leaving the dialyzer, and before traveling through the dialysate circuit, spent dialysate can travel past outlet filter 64. Check valve 65 can be used to ensure that any fluid added to the dialysate circuit cannot travel past dialyzer connector 15 and into the dialyzer, but instead must travel through the dialysate circuit, sorbent cartridge 19, and microbial filter 13 to reach the dialyzer inlet at dialyzer connector 14. Sample and pressure relief port 70 can be used to ensure that the pressure within the dialysate circuit does not build up and to obtain any dialysate samples as may be required. The ultrafiltrate pump 41 through connector 29 can be used to pump fluid volume out of the dialysate circuit and into waste reservoir 11, and therefore cause a net removal of fluid from the patient when the rate of pump 41 is greater than the combined rates of water pump 20 and infusate pump 37. Water pump 20 can be used to add water to the dialysate circuit for purposes of sodium control of the dialysate. In any embodiment of the first, second and third aspects of the invention, blood leak detector 48 can be used to detect if blood is leaking across the dialyzer (not shown). In any embodiment of the first, second and third aspects of the invention, a chemical sensor line 50 can be used during dialysis to detect properties of the regenerated dialysate after passing through the sorbent cartridge 19. Chemical sensor valve 51 can be opened to draw off a small amount of the regenerated dialysate. The regenerated dialysate will then travel through carbon dioxide sensor 52, pH sensor 53 and ammonia sensor 54. In any embodiment of the first, second and third aspects of the invention, carbon dioxide sensor 52, pH sensor 53 and ammonia sensor 54 can be contained in the main dialysate flow path between the outlet of sorbent cartridge 19 and the dialyzer inlet at connector 14. Ultrafiltrate pump recirculation connector 71 and water pump recirculation connector 72 can be used to connect the ultrafiltrate pump 41 by means of ultrafiltrate connector 29 and water pump 20 by means of water pump connector 57 during rinsing, cleaning or disinfection and source water reservoir (not shown) to the system.

Through all phases of filling, flushing, and priming the system, as well as during actual therapy, fluid can be directed to degassing vessel 38 to remove dissolved and undissolved gases from the dialysate. Degassing pump 66 can create a vacuum in the degassing vessel 38. The lower pressure created in the degassing vessel 38 can cause dissolved gasses to come out of solution. Gas removal apparatus 67 can draw the gasses out of the degassing vessel 38 to leave the dialysate circuit. Gas removal pump 78 provides the driving force to remove the gases from the dialysate circuit. Vacuum pressure sensor 68 can be used to ensure that a proper vacuum is being created, and degas flow restrictor 69 constricts the flow to cause a vacuum in degas vessel 38 by action of gas removal pump 78.

Figure 5:
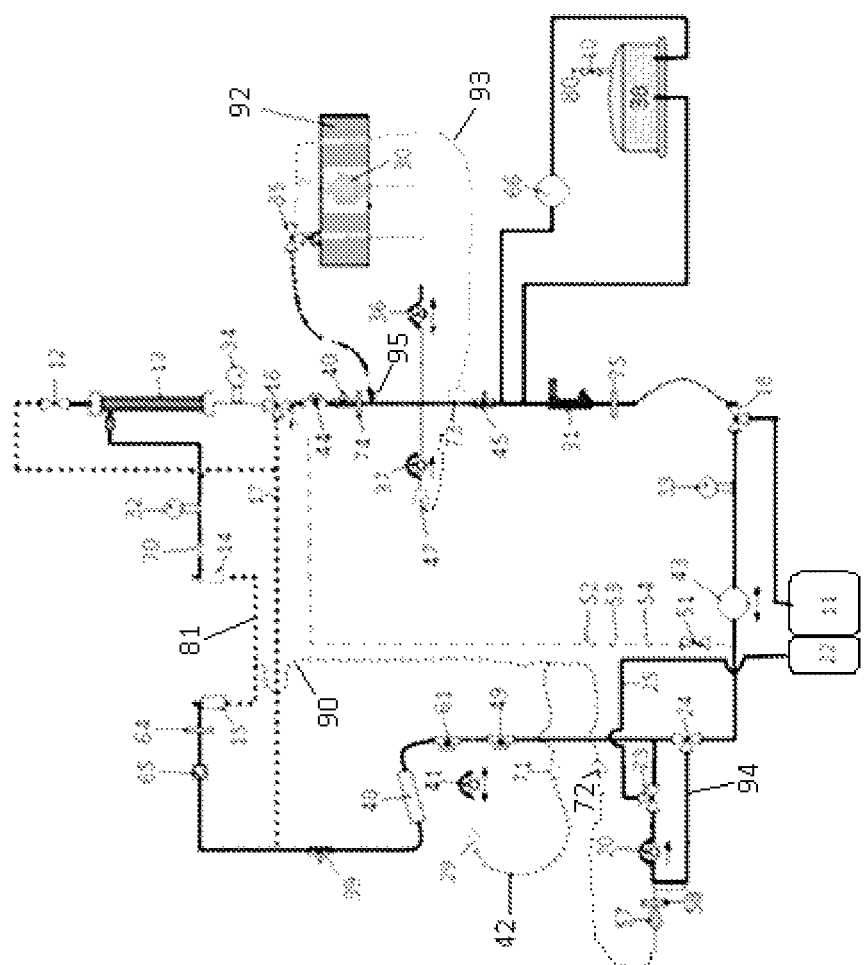
FIG. 5 shows a schematic of a dialysate circuit configured for disinfection and sterilization.

After therapy is complete, the user can disconnect the sorbent cartridge 19 that is now filled with dialysate solution, the dialyzer (not shown), the source water reservoir 21, the infusate source 26, bicarbonate reservoir 27, sodium chloride reservoir 28, and the ultrafiltrate reservoir (not shown) from the ultrafiltrate reservoir connector 29 in embodiments where the ultrafiltrate reservoir is not also the waste reservoir. In any embodiment of the first, second and third aspects of the invention, more than one of these components can be provided as needed. FIG. 5 shows the dialysate circuit with these portions removed. Citric acid cartridge 30 can be attached to the dialysate circuit in place of the sodium chloride reservoir 28 and bicarbonate reservoir 27 shown in FIG. 3. In any embodiment of the first, second and third aspects of the invention, citric acid cartridge holder 92 can hold the citric acid cartridge 30. The dialysate circuit can be drained by directing drain valve 18 to drain to the waste reservoir 11, and allowing air to pass into the circuit through vent valve 10 so that the fluid is pushed into the waste reservoir 11.

Once the dialysate circuit is drained, the dialysate circuit can be flushed using the purified water from the rinse water reservoir 22 of the first, second and third aspects of the invention. The lines of the dialysate circuit can be filled by opening the valves to each portion of the dialysate circuit, while air is removed by degas vessel 38 and vent 10. First, the dialyzer bypass line 17 can be flushed by controlling dialyzer bypass valve 16 to direct purified water from the rinse water reservoir 22 into the dialyzer bypass line 17 while microbial filter valve 12 is closed. Next, the dialyzer flow path can be flushed by switching dialyzer bypass valve 16 to allow purified water from the rinse water reservoir 22 to pass through the dialyzer flow path 81 via the portion of jumper line 90 between dialyzer connectors 14 and 15. Next, the microbial filter 13 can be flushed by switching microbial filter valve 12 to allow rinse water to flow through the microbial filter 13. The ultrafiltration line 42 can be flushed by utilizing ultrafiltration pump 41 to draw purified water into the ultrafiltration lines 42. The cation infusate line 96 can be flushed by utilizing pump 37 to pass water through cation connector 47 and recirculation connector 73. The salt path 95 can be flushed through the cartridge pump 36 through jumper recirculation assembly 92.

The draining and flushing process can be repeated multiple times in order to ensure that the dialysate circuit is sufficiently rinsed. In any embodiment of the first, second and third aspects of the invention, there may be a predetermined number of times the dialysate circuit needs to be flushed in order to properly proceed. In any embodiment of the first, second and third aspects of the invention, the draining and flushing process can be repeated 2, 3, 4, 5, 6 or more times. In any embodiment of the first, second and third aspects of the invention, conductivity measurements may be taken of the fluid in the dialysate circuit, and the flushing can be considered complete when the conductivity drops below a predetermined value. In any embodiment of the first, second and third aspects of the invention, one or more of sensors 39, 40, and 45 can be conductivity sensors. In any embodiment of the first, second and third aspects of the invention, one or more of the sensors 39, 40, and 45 can be temperature sensors. The exact placement of conductivity sensors or temperature sensors is flexible; their positions in FIG. 5 can be changed without detracting from the invention. In any embodiment of the first, second and third aspects of the invention, the draining step can be omitted. Instead, fluid is allowed to move to the drain reservoir during flushing of the system. The system is flushed by adding water to the system and allowing the excess fluid into the drain. However, this process may consume more water for flushing than if the system is completely drained before flushing.

Once the dialysate circuit is properly flushed, the pumps and valves can be controlled to direct purified water from the rinse water reservoir 22 into the citric acid cartridge 30, in order to fill the system with a citric acid solution for cleaning and disinfection. In any embodiment of the first, second and third aspects of the invention, citric acid cartridge 30 can be filled with dry citric acid, such as citric acid monohydrate. Other forms of citric acid, for example anhydrous citric acid, or citric acid dihydrate are contemplated by the first, second and third aspects of the invention. In any aspect of the infection, citric acid cartridge 30 can be filled with a liquid concentrate form of citric acid. One skilled in the art will understand that citric acid cartridge 30 can contain an amount of a dry or liquid concentrate form of citric acid such that when the citric acid is dissolved into the prime volume of the dialysate flow path by the water from rinse water reservoir 22, a citric acid solution with a predetermined concentration is produced. That is, the concentration of citric acid in the disinfection solution will be equal to the amount of citric acid in the citric acid cartridge 30 divided by the total volume of the disinfection solution. In any embodiment of the first, second and third aspects of the invention, the concentration of citric acid produced can be 2%. Other concentrations of citric acid are contemplated by the first, second and third aspects of the invention, including between 1% and 15%, between 2% and 10%, and between 5% and 13%. In any embodiment of the first, second and third aspects of the invention, citric acid cartridge 30 can be filled with a citric acid solution that is diluted as the citric acid solution enters the dialysate flow path. Cartridge pump 36 can draw the purified water from the rinse water reservoir 22 into the citric acid cartridge 30 when diverter valve 35 is open to the citric acid cartridge 30.

The dialysate circuit can then undergo the disinfection process. The citric acid solution can be circulated in the dialysate circuit while the solution is heated by heater 31. In any embodiment of the first, second and third aspects of the invention, the fluid can be heated to 85° C. In any embodiment of the first, second and third aspects of the invention, the fluid can be heated to a different temperature. In any embodiment of the first, second and third aspects of the invention, the citric acid solution can be heated to at least 85° C. In any embodiment of the first, second and third aspects of the invention, the citric acid solution can be heated to between any of 60-100° C., 60-75° C., 65-90° C., 75-85° C. or 85-100° C. In any embodiment of the first, second and third aspects of the invention, heater 31 may have a heater control sensor (not shown) to control the operation of the heater 31. In any embodiment of the first, second and third aspects of the invention, the heater 31 may also have a heater over temperature switch (not shown), which can automatically shut down the heater 31 in the event of overheating. As the solution heats, the liquid expands and gas can be generated, increasing the pressure in the dialysate circuit. Fluid can be drawn to the degassing vessel 38 by vacuum pump 66, and gas can leave the system through the vent 10 in degassing vessel 38 as represented by arrow 80. A small volume of fluid can be released from the flow path through valve 18 to reservoir 11 to relieve pressure increases due to thermal expansion of the solution as the solution heats. If the fluid level drops, the reverse drain valve 23 can be pulsed, which can draw more purified water from the rinse water reservoir 22 into the dialysate circuit to maintain a minimum fluid level. The valves can be controlled during the heating process so that the hot fluid flows through all of the lines, similarly to the flushing and rinsing cycles explained above. Temperatures may be monitored with temperature sensors at various locations throughout the circuit, such as temperature sensors 39, 45 and 40. Dialysate inlet pressure sensor 32, sorbent pressure sensor 33, and microbial filter pressure sensor 34 can be utilized to ensure that an appropriate pressure exists throughout the dialysate circuit. The appropriate pressure is sufficient to ensure that the fluid in the circuit does not boil, yet remains below the working strength of the dialysate flow path components and materials of construction.

In any embodiment of the first, second and third aspects of the invention, the disinfection process can be continued for 5 minutes while the fluid at all locations in the dialysate circuit is above a predetermined minimum effective disinfection temperature. In any embodiment of the first, second and third aspects of the invention, the predetermined temperature can be at least 85° C. In any embodiment, the predetermined temperature can be between any of 60-100° C., 65-90° C., 75-85° C. or 85-95° C. In any embodiment of the first, second and third aspects of the invention, the disinfection process can be longer or shorter. In any embodiment of the first, second and third aspects of the invention, the disinfection process can be continued for 5 minutes. In any embodiment of the first, second and third aspects of the invention, the disinfection process can be continued for between any of 1-20 minutes or longer, 3-10 minutes, 7-17 minutes or longer.

To make use of the water management system of the first, second and third aspects of the invention easier, the valves may be operated by a programmable controller or computer system that can be programmed to regulate flow through the valves and into and out of the reservoirs. An optical sensor, photocell or other flow sensing apparatus 44, 61, and 49 may detect the flow of fluid through any two points in the dialysate circuit. For example, an optical fluid flow device can be provided for measuring flow wherein the device includes sensors positioned in any one of the flow paths between the reservoirs, in the connectors, or in the valves or valve assemblies. In any embodiment of the first, second and third aspects of the invention, the optical fluid sensors described above can be connected to an interferometer associated with an opto-electronic demodulator which has an output signal representing the flow rate between the two sensed areas. The flow-responsive element can be made of a wide variety of materials having the desired properties known to those of ordinary skill in the art. In any embodiment of the first, second and third aspects of the invention, a turbine type flow sensor can be used. A turbine flow sensor comprises a turbine in the flow path. The flow of fluid through the flow path causes the turbine to rotate at a speed proportional to the velocity of the fluid. An optical sensor can generate a pulse frequency corresponding to the angular velocity of the turbine rotor, which can be translated into a fluid velocity.

Figure 6:
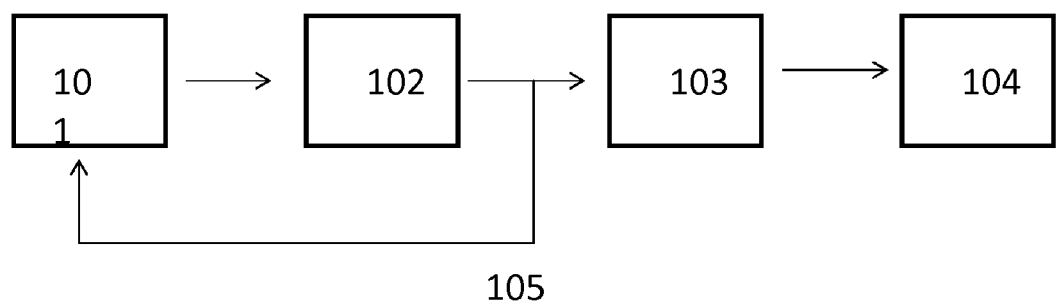
FIG. 6 is a flow diagram showing the method of rinsing, and cleaning and disinfecting the dialysis system using purified water from a rinse water reservoir.

FIG. 6 shows a flow chart depicting the cleaning and disinfection process of the first, second and third aspects of the invention. The first step is to drain the dialysate circuit of the dialysate 101. The second step is to flush the dialysate circuit 102 by rinsing the dialysate circuit with water from the rinse water reservoir. In any embodiment of the first, second and third aspects of the invention, the steps of draining the dialysate circuit 101 and flushing the dialysate circuit 102 can be repeated once or multiple times as represented by arrow 105. In any embodiment of the first, second and third aspects of the invention, the steps of draining the dialysate circuit 101 and flushing the dialysate circuit 102 can be repeated a pre-set number of times. In any embodiment of the first, second and third aspects of the invention, conductivity measurements may be taken as explained above, and the steps of draining the dialysate circuit 101 and flushing the dialysate circuit 102 can be repeated until the conductivity measurements show that the level of impurities in the fluid are below a pre-set point. After the dialysate circuit is flushed 102, the dialysate circuit can be filled with purified water from the rinse water reservoir 103. In any embodiment of the first, second and third aspects of the invention, the purified water from the rinse water reservoir can be directed through a citric acid cartridge in order to fill the system with a citric acid solution. The fluid is then circulated while the fluid is heated 104 to complete the disinfection process.

The rinse water reservoir 22 of the first, second and third aspects of the invention, as shown in FIG. 5, can also be disinfected periodically. The rinse water reservoir 22 can be constructed so that the rinse water reservoir 22 can be detached from the rest of the dialysis system. The rinse water reservoir 22 can then be cleaned with bleach or other cleaning agents. This process can be done either after a set amount of time, such as weekly or biweekly, or after a set amount of dialysis sessions. In any embodiment of the first, second and third aspects of the invention, the cleaning may not be necessary between each dialysis session in order to maintain sufficient hygiene.

In any embodiment of the first, second and third aspects of the invention, the filling, cleaning and disinfection processes can be automatically accomplished by the programmable controller or computer system. The user may initiate the pre-dialysis draining of the citric acid solution, and the controller may automatically operate the pumps and valves to accomplish the draining as described above. The controller can then operate the pumps and valves as described above to flush the dialysate circuit and fill the rinse water reservoir with purified water. The controller can also automatically prime the dialysate circuit with a physiologically compatible saline solution.

After dialysis, and after the user has disconnected the dialyzer, sorbent cartridge, source water reservoir, infusate source, bicarbonate source, sodium chloride source, and the ultrafiltrate reservoir in embodiments of the first, second, or third aspects of the invention where the ultrafiltrate reservoir is not also the waste reservoir, the controller can automatically start the cleaning and disinfection process. The controller can automatically operate the pumps and valves as described above in order to drain the spent dialysate from the dialysate circuit, flush the dialysate circuit with purified water from the rinse water reservoir and fill the dialysate circuit with a citric acid solution. The controller can also automatically heat the fluid to the desired temperature for disinfection.

It will be apparent to one skilled in the art that various combinations and/or modifications and variations can be made in the dialysis system depending upon the specific needs for operation. Moreover features illustrated or described as being part of an aspect of the invention can be included in the aspect of the invention, either alone or in combination.

I claim:

1. A water management system for use in sorbent dialysis comprising:
a rinse water reservoir configured to receive purified water obtained from a sorbent cartridge containing one or more sorbent materials, wherein the rinse water reservoir is fluidly connectable to a rinse water reservoir line, the rinse water reservoir line fluidly connectable to a dialysate circuit by one or more valves; wherein the rinse water reservoir line is fluidly connectable to the dialysate circuit at a position upstream of the sorbent cartridge;
a water source, wherein the one or more valves are fluidly connectable to the water source and the sorbent cartridge,
wherein water from the water source is directed to the sorbent cartridge and the water is purified by the sorbent cartridge, and is stored in the rinse water reservoir; and
a drain, wherein the drain is fluidly connectable to at least one drain valve; wherein the at least one drain valve is fluidly connectable to the dialysate circuit.

2. The water management system of claim 1 wherein the water management system is part of a controlled compliant dialysate circuit.

3. The water management system of claim 1, wherein the water source is a source water reservoir.

4. The water management system of claim 1, wherein the drain comprises a waste reservoir.

5. The water management system of claim 1 further comprising a microbial filter positioned in the fluid flow path after the sorbent cartridge and before a dialyzer, wherein the microbial filter is fluidly connectable to the rinse water reservoir.

6. The water management system of claim 1 further comprising one or more pumps to direct a fluid in the fluid flow path.

7. The water management system of claim 6 further comprising a programmable controller to control the one or more valves in the dialysate circuit, drain valve, and pumps.

8. The water management system in claim 1, wherein the sorbent cartridge receives water used in flushing the dialysate circuit.

9. The water management system in claim 1, wherein the sorbent cartridge is positioned downstream to the water source.

10. The water management system in claim 1, wherein the water from the water source is further directed through a microbial filter, and wherein the purified water is free from chemical and microbiological contamination.

11. The water management system of claim 1, further comprising a citric acid cartridge fluidly connectable to the dialysate circuit at a position downstream of the rinse water reservoir line.

12. A method of filling a rinse water reservoir of a water management system comprising the step of:

directing water from a water source, through a sorbent cartridge, and then into the rinse water reservoir;

wherein the rinse water reservoir is configured to receive purified water obtained from the sorbent cartridge containing one or more sorbent materials, wherein the rinse water reservoir is fluidly connectable to a rinse water reservoir line, the rinse water reservoir line fluidly connectable to a dialysate circuit by one or more valves; wherein the rinse water reservoir line is fluidly connectable to the dialysate circuit at a position upstream of the sorbent cartridge;

wherein the water management system comprises the water source, wherein the one or more valves are fluidly connectable to the water source and the sorbent cartridge, wherein the method comprises directing water from the water source to the sorbent cartridge, wherein the water is purified by the sorbent cartridge, and is stored in the rinse water reservoir; and wherein the water management system comprises a drain, wherein the drain is fluidly connectable to at least one drain valve; wherein the at least one drain valve is fluidly connectable to the dialysate circuit.

13. The method of claim 12 further comprising the step of directing water through a microbial filter prior to the step of directing water into the rinse water reservoir.

14. The method of claim 12 wherein the water from the water source travels through the dialysate circuit defining a fluid flow path before flowing into the rinse water reservoir.

15. The method of claim 14 further comprising the step of directing water from the water source through lines of a dialysis system and into the drain prior to the step of directing water from the water source through the sorbent cartridge and into the rinse water reservoir.

16. The method of claim 15 wherein the step of directing water from the water source through the lines of the dialysis system and into the drain is repeated multiple times prior to directing water into the rinse water reservoir.

17. The method of claim 15 wherein the step of directing water from the water source through the lines of the dialysis system and into the drain is repeated a pre-set number of times.

18. The method of claim 17 wherein the step of directing water from the water source through the lines of the dialysis system and into the drain is repeated any of 2, 3, 4, 5 or 6 times.

19. The method of claim 15 further comprising the step of taking a conductivity measurement after directing water from the water source through the lines of the dialysis system and into the drain; and wherein the step of directing water from the water source through the lines of the dialysis system and into the drain is repeated until the conductivity measurement shows a conductivity below a pre-set number.

20. The method of claim 12 wherein a programmable controller operates one or more pumps and the one or more valves to direct the filling of the rinse water reservoir.

21. A method of disinfecting a dialysis system comprising the steps of:

directing purified water from a rinse water reservoir through lines of the dialysis system, wherein the purified water is produced by having water pass through a sorbent cartridge prior to the purified water being placed in the rinse water reservoir; and circulating heated purified water through the dialysis system;

wherein the rinse water reservoir is configured to receive purified water obtained from the sorbent cartridge containing one or more sorbent materials, wherein the rinse water reservoir is fluidly connectable to a rinse water reservoir line, the rinse water reservoir line fluidly connectable to a dialysate circuit by one or more valves; wherein the rinse water reservoir line is fluidly connectable to the dialysate circuit at a position upstream of the sorbent cartridge;

wherein the dialysis system comprises a water source, wherein the one or more valves are fluidly connectable to the water source and the sorbent cartridge, wherein water from the water source is directed to the sorbent cartridge and the water is purified by the sorbent cartridge, and is stored in the rinse water reservoir; and wherein the dialysis system comprises a drain, wherein the drain is fluidly connectable to at least one drain valve; wherein the at least one drain valve is fluidly connectable to the dialysate circuit.

22. The method of claim 21 further comprising the steps of:

attaching a citric acid cartridge to the dialysis system;

directing water from the rinse water reservoir through the citric acid cartridge to create a citric acid solution; and heating the citric acid solution and circulating the citric acid solution through the lines of the dialysis system.

23. The method of claim 22, wherein the dialysis system is heated to a temperature between any of 60-100° C., 60-75° C., 65-90° C., 75-85° C. or 85-100° C. while circulating the citric acid solution.

24. The method of claim 21 further comprising the step of blowing out the lines of the dialysis system with air prior to directing purified water from the rinse water reservoir through the lines of the dialysis system.

25. The method of claim 22 wherein the citric acid cartridge contains dry citric acid.

26. The method of claim 25 wherein the citric acid cartridge contains a predetermined amount of citric acid, and further comprising the step of dissolving the dry citric acid with the purified water directed through the citric acid cartridge to create a citric acid solution of a predetermined concentration.

* * * * *